United States Patent
Pui et al.

(10) Patent No.: US 7,498,063 B2
(45) Date of Patent: *Mar. 3, 2009

(54) HIGH MASS THROUGHPUT PARTICLE GENERATION USING MULTIPLE NOZZLE SPRAYING

(75) Inventors: David Y. H. Pui, Plymouth, MN (US); Da-Ren Chen, Creve Coeur, MO (US)

(73) Assignee: Regents of the University of Minnesota, Minneapolis, MN (US)

( * ) Notice: Subject to any disclaimer, the term of this patent is extended or adjusted under 35 U.S.C. 154(b) by 784 days.

This patent is subject to a terminal disclaimer.

(21) Appl. No.: 10/889,341

(22) Filed: Jul. 12, 2004

(65) Prior Publication Data

US 2004/0241315 A1 Dec. 2, 2004

Related U.S. Application Data

(63) Continuation of application No. 09/858,865, filed on May 16, 2001, now Pat. No. 6,764,720.

(60) Provisional application No. 60/204,451, filed on May 16, 2000.

(51) Int. Cl.
*B05D 1/04* (2006.01)
(52) U.S. Cl. .................. 427/479; 427/475; 427/483; 427/485
(58) Field of Classification Search ............... None
See application file for complete search history.

(56) References Cited

U.S. PATENT DOCUMENTS

| | | | |
|---|---|---|---|
| 3,521,125 A | 7/1970 | Nelson | |
| 3,608,823 A | 9/1971 | Buschor | |
| 3,654,534 A | 4/1972 | Fischer | |
| 3,905,330 A | 9/1975 | Coffee | |
| 4,002,777 A | 1/1977 | Juvinall et al. | |
| 4,039,145 A | 8/1977 | Felici et al. | |
| 4,265,641 A | 5/1981 | Natarajan | |
| 4,328,940 A | 5/1982 | Malcolm | |
| 4,414,603 A | 11/1983 | Masuda | |
| 4,476,515 A | 10/1984 | Coffee | |
| 4,578,290 A | 3/1986 | Koman et al. | |
| 4,634,057 A | 1/1987 | Coffee et al. | |
| 4,659,012 A | 4/1987 | Coffee | |
| 4,748,043 A * | 5/1988 | Seaver et al. | 427/482 |
| 4,749,125 A | 6/1988 | Escallon et al. | |
| 4,795,330 A | 1/1989 | Noakes et al. | |
| 4,846,407 A | 7/1989 | Coffee et al. | |
| 4,945,050 A | 7/1990 | Sanford et al. | |
| 4,946,899 A | 8/1990 | Kennedy et al. | |
| 5,036,006 A | 7/1991 | Sanford et al. | |
| 5,044,564 A | 9/1991 | Sickles | |
| 5,066,587 A | 11/1991 | Jones et al. | |
| 5,091,205 A | 2/1992 | Fan | |
| 5,100,792 A | 3/1992 | Sanford et al. | |
| 5,120,657 A | 6/1992 | McCabe et al. | |
| 5,141,131 A | 8/1992 | Miller, Jr. et al. | |
| 5,149,655 A | 9/1992 | McCabe et al. | |
| 5,179,022 A | 1/1993 | Sanford et al. | |
| 5,204,253 A | 4/1993 | Sanford et al. | |
| 5,219,746 A | 6/1993 | Brinegar et al. | |
| 5,222,663 A | 6/1993 | Noakes et al. | |
| 5,240,842 A | 8/1993 | Mets | |
| 5,247,842 A | 9/1993 | Kaufman et al. | |
| 5,354,556 A | 10/1994 | Sparks et al. | |
| 5,371,015 A | 12/1994 | Sanford et al. | |
| 5,433,865 A | 7/1995 | Laurent | |
| 5,457,041 A | 10/1995 | Ginaven et al. | |
| 5,475,228 A | 12/1995 | Palathingal | |
| 5,478,744 A | 12/1995 | Sanford et al. | |
| 5,506,125 A | 4/1996 | McCabe et al. | |
| 5,516,670 A | 5/1996 | Kuehnle et al. | |
| 5,525,510 A | 6/1996 | McCabe et al. | |
| 5,584,807 A | 12/1996 | McCabe | |
| 5,621,605 A | 4/1997 | Inaba et al. | |
| 5,655,517 A | 8/1997 | Coffee | |
| 5,683,556 A | 11/1997 | Nomura et al. | |

(Continued)

FOREIGN PATENT DOCUMENTS

CA 2 435 721 8/2002

(Continued)

OTHER PUBLICATIONS

Jouyban et al., "A simple relationship between dielectric constant of mixed solvents with solvent composition and temperature," 2004, Int. Journ. Of Pharamceutics, 269:353-360.

(Continued)

*Primary Examiner*—Frederick J Parker
(74) *Attorney, Agent, or Firm*—Mueting Raasch & Gebhardt, P.A.

(57) ABSTRACT

Spraying apparatus and methods that employ multiple nozzle structures for producing multiple sprays of particles, e.g., nanoparticles, for various applications, e.g., pharmaceuticals, are provided. For example, an electrospray dispensing device may include a plurality of nozzle structures, wherein each nozzle structure is separated from adjacent nozzle structures by an internozzle distance. Sprays of particles are established from the nozzle structures by creating a nonuniform electrical field between the nozzle structures and an electrode electrically isolated therefrom.

39 Claims, 14 Drawing Sheets

U.S. PATENT DOCUMENTS

| | | |
|---|---|---|
| 5,685,482 A | 11/1997 | Sickles |
| 5,702,754 A | 12/1997 | Zhong |
| 5,807,436 A | 9/1998 | Stachelhaus et al. |
| 5,813,614 A | 9/1998 | Coffee |
| 5,837,313 A | 11/1998 | Ding et al. |
| 5,846,595 A | 12/1998 | Sun et al. |
| 5,866,400 A | 2/1999 | Palsson et al. |
| 5,873,523 A * | 2/1999 | Gomez et al. ............... 239/3 |
| 5,897,911 A | 4/1999 | Loeffler |
| 5,915,377 A | 6/1999 | Coffee |
| 5,968,091 A * | 10/1999 | Pinchuk et al. ............ 623/1.16 |
| 5,973,904 A | 10/1999 | Pui et al. |
| 5,980,972 A | 11/1999 | Ding |
| 5,992,244 A | 11/1999 | Pui et al. |
| 6,068,199 A | 5/2000 | Coffee |
| 6,074,688 A | 6/2000 | Pletcher et al. |
| 6,093,557 A | 7/2000 | Pui et al. |
| 6,096,070 A | 8/2000 | Ragheb et al. |
| 6,105,571 A | 8/2000 | Coffee |
| 6,105,877 A | 8/2000 | Coffee |
| 6,120,847 A | 9/2000 | Yang et al. |
| 6,126,086 A | 10/2000 | Browner et al. |
| 6,143,037 A | 11/2000 | Goldstein et al. |
| 6,143,370 A | 11/2000 | Panagiotou et al. |
| 6,145,391 A | 11/2000 | Pui et al. |
| 6,207,195 B1 | 3/2001 | Walsh et al. |
| 6,251,136 B1 | 6/2001 | Guruwaiya et al. |
| 6,252,129 B1 | 6/2001 | Coffee |
| 6,277,448 B2 | 8/2001 | Strutt et al. |
| 6,318,640 B1 | 11/2001 | Coffee |
| 6,364,903 B2 | 4/2002 | Tseng et al. |
| 6,368,658 B1 | 4/2002 | Schwarz et al. |
| 6,386,195 B1 | 5/2002 | Coffee |
| 6,399,362 B1 | 6/2002 | Pui et al. |
| 6,419,692 B1 | 7/2002 | Yang et al. |
| 6,419,745 B1 | 7/2002 | Burkett et al. |
| 6,457,470 B1 | 10/2002 | Coffee |
| 6,517,888 B1 | 2/2003 | Weber |
| 6,579,573 B2 | 6/2003 | Strutt et al. |
| 6,595,208 B1 | 7/2003 | Coffee et al. |
| 6,632,671 B2 | 10/2003 | Unger |
| 6,645,569 B2 | 11/2003 | Cramer et al. |
| 6,669,980 B2 | 12/2003 | Hansen |
| 6,670,607 B2 | 12/2003 | Wood et al. |
| 6,684,879 B1 | 2/2004 | Coffee et al. |
| 6,737,463 B2 | 5/2004 | Yadav et al. |
| 6,743,463 B2 | 6/2004 | Weber et al. |
| 6,746,869 B2 | 6/2004 | Pui et al. |
| 6,764,720 B2 | 7/2004 | Pui et al. |
| 6,861,088 B2 | 3/2005 | Weber et al. |
| 6,933,331 B2 | 8/2005 | Yadav et al. |
| 6,989,169 B2 | 1/2006 | Ripoll et al. |
| 7,193,124 B2 | 3/2007 | Coffee |
| 7,247,338 B2 | 7/2007 | Pui |
| 7,279,322 B2 | 10/2007 | Pui et al. |
| 2002/0007869 A1 | 1/2002 | Pui |
| 2002/0065553 A1 | 5/2002 | Weber |
| 2002/0150669 A1* | 10/2002 | Pui et al. ............... 427/2.1 |
| 2002/0151004 A1 | 10/2002 | Craig |
| 2003/0143315 A1 | 7/2003 | Pui et al. |
| 2003/0161937 A1 | 8/2003 | Leiby et al. |
| 2003/0185964 A1 | 10/2003 | Weber et al. |
| 2003/0236514 A1 | 12/2003 | Schwarz |
| 2004/0069632 A1 | 4/2004 | Ripoll et al. |
| 2004/0081745 A1 | 4/2004 | Hansen |
| 2004/0161498 A1 | 8/2004 | Ripoll et al. |
| 2004/0177807 A1 | 9/2004 | Pui et al. |
| 2004/0200729 A1 | 10/2004 | Boulais et al. |
| 2004/0234748 A1 | 11/2004 | Stenzel |
| 2005/0015046 A1 | 1/2005 | Weber et al. |
| 2005/0023368 A1 | 2/2005 | Valpey, III et al. |
| 2005/0055078 A1 | 3/2005 | Campbell |
| 2005/0064008 A1 | 3/2005 | Bucay-Couto et al. |
| 2005/0074478 A1 | 4/2005 | Ofstead et al. |
| 2005/0075714 A1 | 4/2005 | Cheng et al. |
| 2005/0101020 A1 | 5/2005 | Salem et al. |
| 2005/0116070 A1 | 6/2005 | Ganan Calvo et al. |
| 2005/0149177 A1 | 7/2005 | Weber et al. |
| 2005/0158372 A1 | 7/2005 | O'Leary et al. |
| 2005/0175772 A1 | 8/2005 | Worsham et al. |
| 2005/0222485 A1 | 10/2005 | Shaw et al. |
| 2005/0277577 A1 | 12/2005 | Hunter et al. |
| 2006/0002973 A1 | 1/2006 | Barry et al. |
| 2006/0024810 A1 | 2/2006 | Khadkikar et al. |
| 2006/0038027 A1 | 2/2006 | O'Connor et al. |
| 2006/0057259 A1 | 3/2006 | Ripoll et al. |
| 2006/0062820 A1 | 3/2006 | Gertner et al. |
| 2006/0067968 A1 | 3/2006 | Chudzik et al. |
| 2006/0078922 A1 | 4/2006 | Edwards et al. |
| 2006/0088566 A1 | 4/2006 | Parsonage et al. |
| 2006/0099235 A1 | 5/2006 | Blakstvedt et al. |
| 2006/0100568 A1 | 5/2006 | Tan |
| 2006/0177573 A1 | 8/2006 | Pui |

FOREIGN PATENT DOCUMENTS

| | | |
|---|---|---|
| CA | 2 436 524 | 8/2002 |
| CA | 2520702 | 10/2004 |
| CH | 550 022 A | 6/1974 |
| CN | 1052695 A | 7/1991 |
| CN | 1651604 | 8/2005 |
| DE | 198 46 656 A1 | 4/1999 |
| DE | 199 09 333 A1 | 11/1999 |
| EP | 0 234 841 | 9/1987 |
| EP | 0 258 016 A1 | 3/1988 |
| EP | 0 258 016 B1 | 3/1988 |
| EP | 0 270 356 A2 | 6/1988 |
| EP | 0 405 884 A | 1/1991 |
| EP | 0 429 234 A2 | 5/1991 |
| EP | 0 429 234 A3 | 5/1991 |
| EP | 0 429 234 B1 | 5/1991 |
| EP | 0 434 616 A1 | 6/1991 |
| EP | 0 434 616 B1 | 6/1991 |
| EP | 1 364 718 A1 | 11/2003 |
| ES | 2 180 405 | 2/2003 |
| JP | 6-242273 | 9/1994 |
| JP | 2004 531365 | 10/2004 |
| MX | PA03006862 A | 10/2004 |
| WO | WO 91/00915 | 1/1991 |
| WO | WO 91/07487 | 5/1991 |
| WO | WO 93/07465 | 4/1993 |
| WO | 97/13503 | 4/1997 |
| WO | 97 49484 A | 12/1997 |
| WO | WO 98/03267 | 1/1998 |
| WO | WO 98/56894 | 12/1998 |
| WO | WO 99/03517 | 1/1999 |
| WO | WO 99/30812 | 6/1999 |
| WO | WO 99/30835 | 6/1999 |
| WO | WO 99/31019 | 6/1999 |
| WO | WO 01/87491 A | 11/2001 |
| WO | 02/060275 A1 | 8/2002 |
| WO | 02/060591 A1 | 8/2002 |
| WO | 03/028622 | 4/2003 |
| WO | WO 03/082363 A1 | 10/2003 |
| WO | WO 2004/047882 A2 | 6/2004 |
| WO | 2005/074913 A2 | 8/2005 |
| WO | 2006/003504 | 1/2006 |
| WO | 2007/089883 A2 | 8/2007 |

OTHER PUBLICATIONS

Ré. "Formulating Drug Delivery Systems by Spray Drying," 2006. *Drying Technology*. vol. 24, No. 4, pp. 433-446(14).

Salata. "Tools of Nanotechnology: Electrospray," 2005. *Current Nanoscience*, vol. 1, No. 1, pp. 25-33(9).

Shi et al., "Current advances in sustained-release system for parenteral drug delivery," 2005. *Expert Opinion on Drug Delivery*, vol. 2, No. 6. Abstract Only.

Willems et al., "State of the art overview and forecasts based on existing information of nanotechnology in the field of nanomaterials," 2004. *Work Documents on Nanomaterials*. 75 pgs.

Yokoyama et al., "Nanoparticle Technology for the Production of Functional Materials," 2005. *Hosokawa Powder Technology Research Institute*. KONA No. 23.

Young et al. "Phospholipid-Stabilized Nanoparticles of Cyclosporine A by Rapid Expansion from Supercritical to Aqueous Solution," 2003. *AAPS Pharm.SciTech* 5(1) Article 11. pp. 1-16.

www.crititech.com/technology Website dated Jun. 15, 2002, 5 pages.

Adachi et al., "Unipolar and Bipolar Diffusion Charging of Ultrafine Aerosol Particles", *J. Aerosol Sci.*, 16(2):109-123 (1985).

Büscher et al., "Performance of a unipolar 'square wave' diffusion charger with variable nt-product", *J. Aerosol Sci.*, 25(4):651-663 (1994).

Chen et al., "Design and Evalution of a Nanometer Aerosol Differential Mobility Analyzer (Nano-DMA)", *J. Aerosol Sci.*, 29(5/6):497-509 (1998).

Chen et al., "Electrospraying of Conducting Liquids for Mono-dispersed Aerosol Generation in the 4 nm to 1.8 μm Diameter Range", *J. Aerosol Sci.*, 26(6):963-977 (1995).

Chen et al., "Experimental Investigation of Scaling Laws for Electrospraying: Dielectric Constant Effect", *Aerosol Science and Technology*, 27:367-380 (1997).

Fuchs, "On the Stationary Charge Distribution on Aerosol Particles in a Bipolar Ionic Atmosphere", *Geodis:Pura. Appl.*, 56(III):185-193 (1963).

Ganan-Calvo, "Generation of Steady Liquid Microthreads and Micron-Sized Monodisperse Sprays in Gas Streams", *Phys. Rev. Lett.*, 80(2):285-288 (1998).

Ganan-Calvo, "New Microfluidic Technologies to Generate Respirable Aerosols for Medical Application", *J. of Aerosol Sci.*, 30(Suppl. 1):S541-S542 (1999).

Hoppel et al., "The Nonequilibrium Character of the Aerosol Charge Distributions Produced by Neutralizers", *Aerosol Sci. & Technol.*, 12:471-496 (1990).

Lui et al., "On Unipolar Diffusion Charging of Aerosols in the Continuum Regime", *J. Colloid Interface Sci.*, 58(1):142-149 (1977).

Product Literature, "BINKS Electrostatic spray painting equipment", 7 pgs.

Pui et al., "Nanometer Particles: A New Frontier For Multidisciplinary Research", *J. Aerosol Sci.*, 28(4):539-544 (1997).

Pui et al., "Unipolar Diffusion Charging Ultrafine Aerosols", *Aeorosol Sci. Techn.*, 8:173-187 (1988).

Romay et al., "Unipolar Diffusion Charging of Aerosol Particles at Low Pressure", *Aerosol Sci. Techn.*, 15:60-68 (1991).

Romay et al., "On the Combination Coefficient of Positive Ions with Ultrafine Neutral Particles in the Transition and Free-Molecule Regimes", *Aerosol Sci. Techn.*, 17:134-147 (1992).

Romay et al., "Free electron charging of ultrafine aerosol particles", *J. Aerosol Sci.*, 23(7):679-692 (1992).

Rulison et al., "Scale-up of electrospray atomization using linear arrays of Taylor cones", *Rev. of Sci. Instrum.*, American Institute of Physics, New York, 64(3):683-686 (1993).

Songstad et al., "Advances in alternative DNA delivery techniques", *Plant Cell, Tissue and Organ Culture*, 40:1-15 (1995).

Wiedensohler et al., "A novel unipolar charger for ultrafine aerosol particles with minimal particle losses", *J. Aerosol Sci.*, 25(4):639-649 (1994).

\* cited by examiner

HIGH MASS THROUGHPUT PARTICLE GENERATION USING MULTIPLE NOZZLE SPRAYING

CROSS-REFERENCE TO RELATED APPLICATIONS

This application is a continuation application of Ser. No. 09/858,865, filed on May 16, 2001 (now U.S. Pat. No. 6,764,720), which claims the benefit under 35 U.S.C. §119(e) of U.S. Provisional Patent Application No. 60/204,451, filed on May 16, 2000, which are all incorporated herein by reference in their entirety.

STATEMENT OF GOVERNMENT SUPPORT

The invention was made with the support of U.S. Department of Energy grant number DE-FG02-98ER14909. The United States government may have certain rights to the invention.

TECHNICAL FIELD

The present invention relates generally to spray apparatus and methods. More particularly, the present invention pertains to multiple nozzle spray methods and apparatus, e.g., multiple nozzle electrospray methods and apparatus.

BACKGROUND OF THE INVENTION

It has been recognized that microsphere production technology can produce drugs or pharmaceuticals that can be taken up by cells, e.g., cells in an intestinal or stomach wall or lining, and may cross into the bloodstream. Such uptake or absorption into the cell is determined at least in part by the surface chemistry of the microspheres. Uptake of microspheres containing macromolecules, e.g., encapsulated proteins, has also been demonstrated.

Currently in drug production, top-down processes are typically used to produce drug particles. For example, in such processes, particles may be formed using grinding techniques. Further, for example, it has been described that such particles may be formed by removing solvent from a mixture that includes the active ingredient as it is being sprayed into a stream of air, e.g., hot air drying.

Electrohydrodynamic spraying (or electrospray) has been used to produce nanoparticles from, for example, solutions or colloidal suspensions. The electrospray is capable of producing nanoparticles that are 10-100 times smaller than, for example, conventional pneumatic atomization techniques. This size of particles allows product that includes such particles to have 100-10,000 times larger surface area than those produced from the conventional techniques, for a given quantity of spray solution.

The increased surface area forms the basis of enabling technology for various important applications. For example, new chemicals being synthesized as future drug products are decreasing in aqueous solubility to such an extent as to present major delivery and development challenges. If the drug products employ nanoparticles rather than macroparticles, the increased surface area results in a significantly greater dissolution rate and/or higher solubility rate. This may allow for superior and/or even enabling drug delivery. Nanoparticle medicine may increase the bioavailability and speed up the response time of the delivered drug. Thus, nanoparticle technology has the potential to significantly impact the pharmaceutical industry.

As described in U.S. Pat. No. 6,105,571 to Coffee, entitled "Dispensing Device," issued 22 Aug. 2000, particles are generated that may comprise biologically active material, for example, particles may contain matter such as peptides or large biomolecules such as insulin and/or other pharmaceutical components for enabling delivery of an active component into the blood stream. As indicated therein, electrohydrodynamic processes are used to produce particles, but primarily are used to produce fibres or fibre fragments.

One limiting factor in employing electrospray or electrohydrodynamic techniques for particle generation is that generally only a single spray-nozzle dispenser is used that can deliver only a small quantity of solution, e.g., a few μl/min. A major challenge and problem is the inability to increase the mass throughput from such an electrospray device that can produce nanoparticles so that electrohydrodynamic techniques can be used to deliver industrial quantities particles for use in various products.

U.S. Pat. No. 6,105,571 cited above, shows use of multiple nozzles to produce fibres or particles as described therein. However, problems associated with multiple nozzle approaches are not addressed, e.g., the space charge effect of particles produced using electrospray techniques, arcing between nozzles, etc.

SUMMARY OF THE INVENTION

For the above reasons, there is a need in the art for mass throughput apparatus and methods which overcome the problems described above, and other problems as will become apparent to one skilled in the art from the detailed description below. The present invention provides apparatus and methods that produce nanoparticles with high mass throughput, e.g., can produce large quantities of nanoparticles for use in various applications, e.g., pharmaceutical, biological material production for gene therapy, coatings, fabrication processes, etc.

An electrospraying method of the present invention may include one or more of the following features: providing a plurality of nozzle structures, wherein each nozzle structure includes at least one opening defined along a center axis of the nozzle structure and terminating at a dispensing end thereof from which a spray of particles having an electrical charge applied thereto is dispensed; nozzle structures that are separated from adjacent nozzle structures by at least an internozzle distance (L) defined by the distance between center axes of the nozzle structures, wherein the ratio of the internozzle distance (L) to a diameter (D) of the opening at the dispensing end is equal to or greater than 2; dispensing a spray of particles from each of a plurality of nozzle structures by creating a nonuniform electrical field between the dispensing ends from which the sprays are established and an electrode electrically isolated from the dispensing ends; nozzle structures that include a capillary tube comprised of a body portion and a tapered capillary tip at the dispensing end of the capillary tube; nozzle structures that include a tapered portion used to define an opening, wherein at least a part of each of the nozzle structures extends from an integral multiple nozzle structure conductive portion; nozzle structures that include a solid post along a center axis extending through an opening at a dispensing end thereof; dispensing ends of the nozzle structures that are positioned in an x-y plane and have the center axis thereof aligned along the z axis; dispensing a spray of microdroplets including an active ingredient, wherein the electrical charge is concentrated on the active ingredient as the microdroplet evaporates; providing a circular configuration of nozzle structures including an outer multiple nozzle structure ring and one or more inner multiple nozzle structure rings, wherein each of the outer multiple nozzle structure ring and the inner multiple nozzle structure rings are concentric about a center nozzle structure; providing a circular configuration of nozzle structures, wherein each of the nozzle structures of the one or more inner multiple nozzle structure rings are at a substantially equal internozzle distance (L) from adjacent nozzle structures; isolating the dispensing ends of the nozzle structures from one another using separation structures such that a cone jet is allowed to form at the dispensing end of each nozzle structure; dispensing particles that have a nominal diameter of about 1 nanometers to about 2000 nanometers; providing nozzle structures that include at least a first and second opening terminating at the dispensing end of each nozzle structure; providing flows of fluid compositions at the first opening and second opening and establishing a spray of particles from such fluid compositions (e.g., a first fluid composition including an active ingredient and a second fluid composition including a coating component); providing an excipient material and combining the spray of particles with the excipient material; providing a charged pattern and collecting the spray of particles on the charged pattern; dispensing the spray of particles into a container operable for inhalation by a user; and dispensing the spray of particles at a rate in the range of 2 grams/minute to 50 grams/minute.

An apparatus for electrospraying particles according to the present invention may include one or more of the following features: a particle source; a dispensing device configured to receive source material from the particle source, wherein the dispensing device comprises a plurality of nozzle structures; nozzle structures that each include at least one opening defined along a center axis of the nozzle structure and terminating at a dispensing end thereof; nozzle structures that are separated from other adjacent nozzle structures by at least an internozzle distance (L) defined by the distance between center axes of nozzle structures, wherein the ratio of the internozzle distance (L) to a diameter (D) of the opening at the dispensing end is equal to or greater than 2; an electrode isolated from the dispensing end, wherein a nonuniform electrical field is created between the dispensing ends and the electrode such that a spray of particles having an electrical charge applied thereto is dispensed from the dispensing end of each nozzle structure; nozzle structures that include a capillary tube that has a body portion and a tapered capillary tip at the dispensing end of the capillary tube; nozzle structures that include a tapered portion used to form the opening at the dispensing end, wherein at least a part of each of the nozzle structures extend from an integral multiple nozzle structure conductive portion; nozzle structures that include a solid post along a center axis extending through the opening at the dispensing end thereof; dispensing ends of the nozzle structures that are positioned in an x-y plane and have the center axis thereof aligned along the z axis; a circular configuration of nozzle structures including an outer multiple nozzle structure ring and one or more inner multiple nozzle structure rings, wherein each of the outer multiple nozzle structure ring and the inner multiple nozzle structure rings are concentric about a center nozzle structure; a circular configuration of nozzle structures, wherein each of the nozzle structures of the one or more inner multiple nozzle structure rings are at a substantially equal internozzle distance (L) from adjacent nozzle structures; one or more separation structures positioned between nozzle structures and configured such that cone jets are allowed to form at the dispensing end of each nozzle structure; nozzle structures that include at least a first and second opening terminating at the dispensing end of each nozzle structure; a first particle source of at least a first fluid composition including an active ingredient to be dispensed through the first opening and a second particle source of at least a second fluid composition including a coating component to be dispensed through the second opening so as to provide sprays of coated active ingredients; an excipient material provided on a target surface positioned such that the sprays of particles are directed for contact with the excipient material; and a charged pattern positioned such that the sprays of particles is directed for contact with the charged pattern; a container operable by a user for inhalation of contents therein positioned such that the sprays of particles are directed therein.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

The present invention shall first generally be described with reference to FIG. 1. Various embodiments of the present invention shall then be described further with reference to FIGS. 2-17. It will become apparent to one skilled in the art that elements from one embodiment may be used in combination with elements of the other embodiments and that the present invention is not limited to the specific embodiments described herein, but only as described in the accompanying claims.

The present invention provides spraying apparatus and methods that employ multiple nozzle structures for producing multiple sprays of particles, e.g., uniform size nanoparticles. Conventional single nozzle spraying apparatus and methods have been used for producing nanoparticles, however, such apparatus and methods provide a very small throughput that is not suitable for practical production of a large quantity of nanoparticles for applications, e.g., high tech applications such as in the manufacture of medicines, pharmaceuticals, nanostructured materials, etc.

The present invention overcomes such limitations and can provide increased throughput in excess of, for example, 1,000 times conventional methods and apparatus, in a confined space. As such, the present invention makes it possible to produce industrial quantity of particles, e.g., nanoparticles, for such varied applications.

The present invention is directed to apparatus and methods for generating particles, such as, for example, drug nanoparticles, particles for use in depositing materials on or for forming nanostructures, etc. As further described below, methods and apparatus according to the present invention allow for 1,000 to 10,000 times higher mass throughput rate than a single nozzle electrospray apparatus such as that previously described in U.S. Pat. No. 6,093,572 Pui, et. al., entitled "Electrospraying Apparatus and Method for Introducing Material into Cells" issued 25 Jul. 2000, and also described in the papers entitled, "Electrospraying of Conducting Liquids for Dispersed Aerosol Generation in the 4 nm to 1.8 μm Diameter Range" by Chen, et. al., *J. Aerosol Sci.*, Vol. 26, No. 6, pp. 963-977 (1995), and entitled "Experimental Investigation of Scaling Laws for Electrospraying: Dielectric Constant Effect" by Chen, et. al., *Aerosol Science and Technology*, 27:367-380 (1997) which are hereby incorporated in their entirety by reference thereto.

Figure 1:
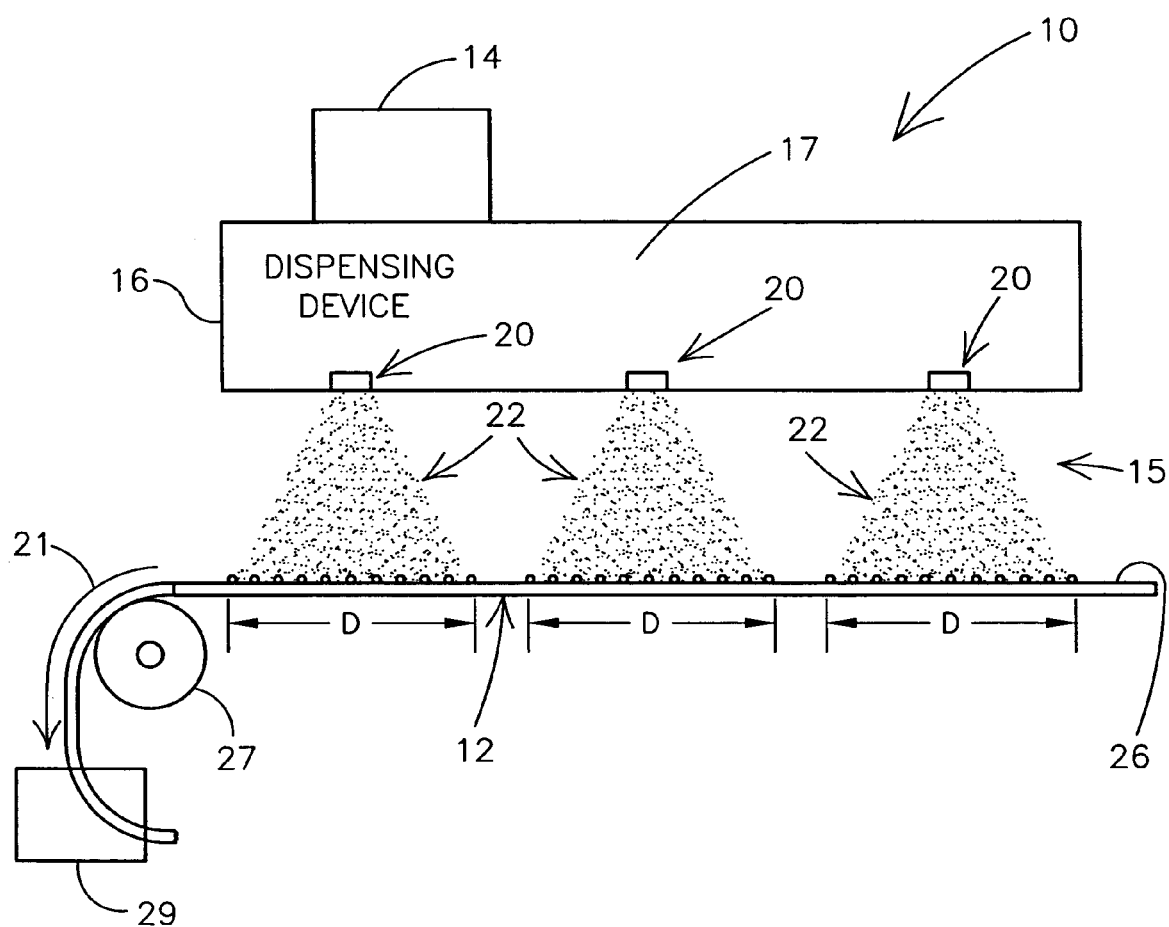
FIG. 1 is a general diagram representative of a particle generator system, e.g., a nanoparticle generator using electrospray techniques, in accordance with the present invention.

As shown in FIG. 1, the present invention provides a particle generator system 10 employing a dispensing device 15 to establish multiple sprays of particles 22. The dispensing device 15 includes a plurality of nozzle structures 20 which receive source material 17 and establish charged sprays of particles 22 forward thereof, e.g., in the direction of target 12.

The dispensing device 15 further includes a source holding apparatus 16 for providing the source material 17 to the plurality of nozzle structures 20 under control of control mechanism 14, e.g. hardware and/or software control. Each nozzle structure 20 is configured to provide a single spray of particles 22. The multiple sprays 22 established forward of each nozzle structure 20 is provided to the target 12. Generally, such sprays 22 established forward of each nozzle structure 20 provided a spray that has a coverage area "D" when the spray 22 reaches the target 12.

The source material 17 held in a source holding apparatus 16 may be any source of material which can be sprayed as described according to the present invention herein. Preferably, the source material 17 is a fluid composition that may include a solution, a suspension, a microsuspension, an emulsion, a microemulsion, a gel, a hydrosol, or any other like fluid compositions that when sprayed according to the present invention results in the generation of particles. For example, such fluid compositions may include a solution of dissolved active ingredients, e.g., drug active ingredients, according to one embodiment of the present invention.

As used herein, an active ingredient refers to any component that provides a useful function when provided in particle form, particularly when provided as nanoparticles. The present invention is particularly beneficial for spraying nanoparticles and also is particularly beneficial for spraying particles including biologically active ingredients.

As such, the term "active ingredient" refers to material which is compatible with and has an effect on the substrate or body with which it is used, such as, for example, drug active ingredients, chemicals elements for forming nanostructures, and elements for film coatings. The term "biologically active ingredient" or "biologically active material or component," is a subset of active ingredient, and refers to material which is compatible with and has an effect (which may, for example, be biological, chemical, or biochemical) on the animal or plant with which it is used and includes, for example, medicants such as medicines, pharmaceutical medicines, and veterinary medicines, vaccines, genetic materials such as polynucleic acids, cellular components, and the like, such as those described below.

As used herein, the term particle, and as such nanoparticle, includes solid, partially solid, and gel like droplets and microcapsules which incorporate solid, partially solid, gel like or liquid matter. As used herein, nanoparticle refers to a particle having a nominal diameter of less than 2000 nm. The present invention is particularly beneficial in spraying nanoparticles having a nominal diameter greater than 1 nanometer (nm), and further preferably having a nominal diameter less than 1000 nm, and more preferably less than 100 nm.

Preferably, the present invention is provided for spraying particles including drug active ingredients, and for simplicity, the remainder of the description herein is primarily provided with respect to such drug active ingredients. However, the present invention is not limited to only such listed applications because mass throughput of nanoparticles is beneficial in various applications as previously described herein.

Further, not only is high mass throughput of nanoparticles provided according to the present invention, but improved uniformity of such nanoparticles is also provided. The standard deviation with respect to mean particle size of particles sprayed according to the present invention is greater than or equal to 2 percent. The present invention is particularly beneficial in spraying nanoparticles that have a standard deviation less than 100 percent, more preferably less than 20 percent, and yet more preferably less than 10 percent.

As described above, the sprays of particles 22 provided from the multiple nozzle structures 20 onto target 12 may be provided for use in various subsequent processes or for various applications. For example, as shown in FIG. 1, target 12 comprises a conveyor surface 26 provided around a moving mechanism 27, e.g., a roller, to provide a manner of collecting a large quantity of particles sprayed thereon. In other words, as conveyor surface 26 moves in the direction of arrow 21, the particles may be removed from the surface 26 and collected in a collection container 29 for later processing and/or usage.

Likewise, although not further described herein, such particles may be deposited directly onto a surface for coating purposes or for forming a layer or structure on a surface. In such cases, the particles would not be removed from the surface, but would form a part thereof.

In one or more embodiments herein, the spray of particles 22 may, for example, be a biologically active ingredient or component that may be applied to a surface or area such as, for example, the surface of the skin or a wound or burn or into a cavity, for example, a body cavity. The body cavity may be any body cavity such as the respiratory system of an animal, e.g., a human being. Such particles may be provided in any number of layers on such a surface or area. Further, the biologically active ingredient or component may be of a substance that adheres to such a surface or area.

Further, the target 12 may be a container for inhalants such as for inhaling therapy applications. As such, the sprays of particles 22 would be provided into the container target 12. In such a manner, the spray of materials may supply comminuted material to a respiratory system of an animal, e.g., a human. Such an inhaling technique may provide nanoparticles to a user orally or nasally.

Biologically active ingredients or components for such applications may be pharmaceutical compounds such as analgesics, antiseptics, antibiotics, antifungals, antibacterials, antiparasitics, debridement agents such as proteolytic enzymes, biological products such as cells, and cytokines for stimulating cytokinetic activity to promote essential cell activities, for example, to stimulate dendritic growth, growth factors such as fibroblast growth factor (FGF), epithelial growth factor (EGF), transforming growth factor (TGF) and others that may be used to promote or otherwise control the sequence of events essential to natural tissue repair, polynucleic acids such as DNA or other genetic material, cells, peptides, or polypeptides, insulin, adjuvants (e.g., an pharmacological agent added to a drug to increase or aid its effect or an immunology agent that increases the antigenic response), immune suppressants, or stimulants, surface binding or surface recognizing agents, surface proteins, and surfactants. The foregoing is only an exemplary list of different active ingredients, and is not to be limiting on the present invention.

Further, the particles generated may be formed of more than one active ingredient and/or other materials by use of multiple nozzles or openings in each of nozzle structures 20 as further described below. For example, a biologically active ingredient may be completely encapsulated within a polymer using the present invention, e.g., a time release encapsulant.

In yet further embodiments according to the present invention, the spray of particles 22 may also be used in a production process to form an orally ingestible capsule, tablet, etc. For example, capsules may include particles that provide for time release of the active ingredient.

Further below, several applications using nanoparticle technology are described in more detail. However, it will be recognized that the present invention may be useful for providing large quantities of nanoparticles for various applications and are not meant to be limited by the specific illustrative and exemplary applications as described further below. Various other applications of particles are also described in U.S. Pat. No. 6,105,571 to Coffee cited above and herein incorporated by reference.

For example, coated drug nanoparticles may be produced according to the present invention. Such drug nanoparticles may include active ingredients coated with suitable excipients. As the present invention provides nanoparticles that have a large surface area relative to other particles (e.g., microspheres), such nanoparticles can be taken up by cellular endocytotic mechanisms, and avoid biochemical barriers to absorption of "bare" molecules through the gut wall, e.g., CYP450A-mediated metabolism and P-glycoprotein-mediated efflux pumping of drugs back into the intestinal lumen.

The ability to use nanoparticles as vehicles for drug absorption may also be applied to protein drugs such as insulin, which are generally very poorly absorbed in the gastrointestinal tract. Uptake of larger spheres containing macromolecules has been performed in recent years, and with the reduction in size to nanoparticles, the effect on absorption should be improved for nanoencapsulated proteins.

Yet further, due to the increased absorptive effects of the nanoparticles generated by the particle generator 10 generally shown in FIG. 1, excipient material, e.g., excipient powders, may be positioned on target surface 12, e.g., conveyor surface 26. The sprays of particles 22 may then be provided for combination with the excipient material on the target 12. Subsequent processing, by any known method or technique, may be used to form a combination of excipient material and active ingredients sprayed thereon into a usable form, e.g., tablets, capsules, etc.

Excipient material refers to any material that may be used with particles generated herein to provide for various functionality, for example, form and consistency of a product in which they are used. For example, excipient materials may include lactose, starch, methylcellulose, polymer materials, or any other suitable materials that provide for various functions, such as, for example, lubrication, useful flow properties such as those that affect capsule or tablet formation, cohesion, texture, taste properties, transport of active ingredients to absorption sites, prevention from acid attack, or other absorption properties, e.g., time release properties.

In addition, for example, a neurological application for the sprays of charged particles 22 is also envisioned, particularly when considering the characteristic growth of neuronal axons to their synaptic target areas. The complex circuits of interconnected neurons in adult organisms are formed during embryonic development by the precise elongation of millions or billions or axonal extensions from neuronal cell bodies through embryonic tissues to synaptic targets. At the tips of growing axons are sensitive motile organelles called growth cones, which interactive with environmental molecules (typically glycoproteins) called guidance cues. Surface receptors on growth cones detect the guidance cues and trigger intracellular changes that specifically enhance or inhibit growth cone advance. The particular pathways taken by different axons are determined by the assortments of guidance cue receptors that are expressed on growth cones of different neuronal types. Binding of guidance cues to their receptors triggers intracellular messages that regulate the cytoskeletal system of actin filaments and microtubules that drives axonal growth. The dynamic assembly and organization of actin filaments and microtubules determine the rates and directions of axonal growth through embryonic tissues.

Many guidance cues are encountered by growth cones as bound to surfaces of extracellular matrices or other cells. Growth cones probably encounter multiple guidance cues simultaneously, and the resultant growth cone behavior reflects the integration of complex temporal and spatial stimuli from guidance cues. Individual growth cones detect guidance cues within a three dimensional space extending 40 or 50 microns from an axon. Thin, transient cytoplasmic projections called filopodia probe outward from a growth cone, and encounter environmental guidance cues via membrane-bound receptors. Little is known about how localized filopodial interactions with guidance cues located many microns from a growth cone are transformed to signals that are relayed to the body of the growth cone, where cytoskeletal organization and dynamics are regulated. The present invention may be used to create small scale patterns of guidance cues to examine how surface bound guidance cues interact with growth cones to determine the behaviors that underlie axonal pathfinding. Such information may provide basic mechanisms that determine the behavior of axonal growth cones during embryonic and fetal development. Further, such information may be useful in devising clinical applications to promote axonal regeneration after injuries to nervous tissues.

For example, in another embodiment of the present invention, charged nanoparticles from the sprays of particles 22 can be collected on a substrate having a defined charge pattern formed thereon, e.g., a charged pattern for depositing growth factor active ingredients. For example, such a defined charge pattern may be formed by contact charging or nanoprint procedures. In other words, a charged pattern having an opposite charge of the charged nanoparticles may be formed such that charged nanoparticles provided by the sprays 22 can be collected on the pattern. In such a way, active ingredients of the nanoparticles may be used to provide for growth of neuronal axons to target areas.

Figure 2:
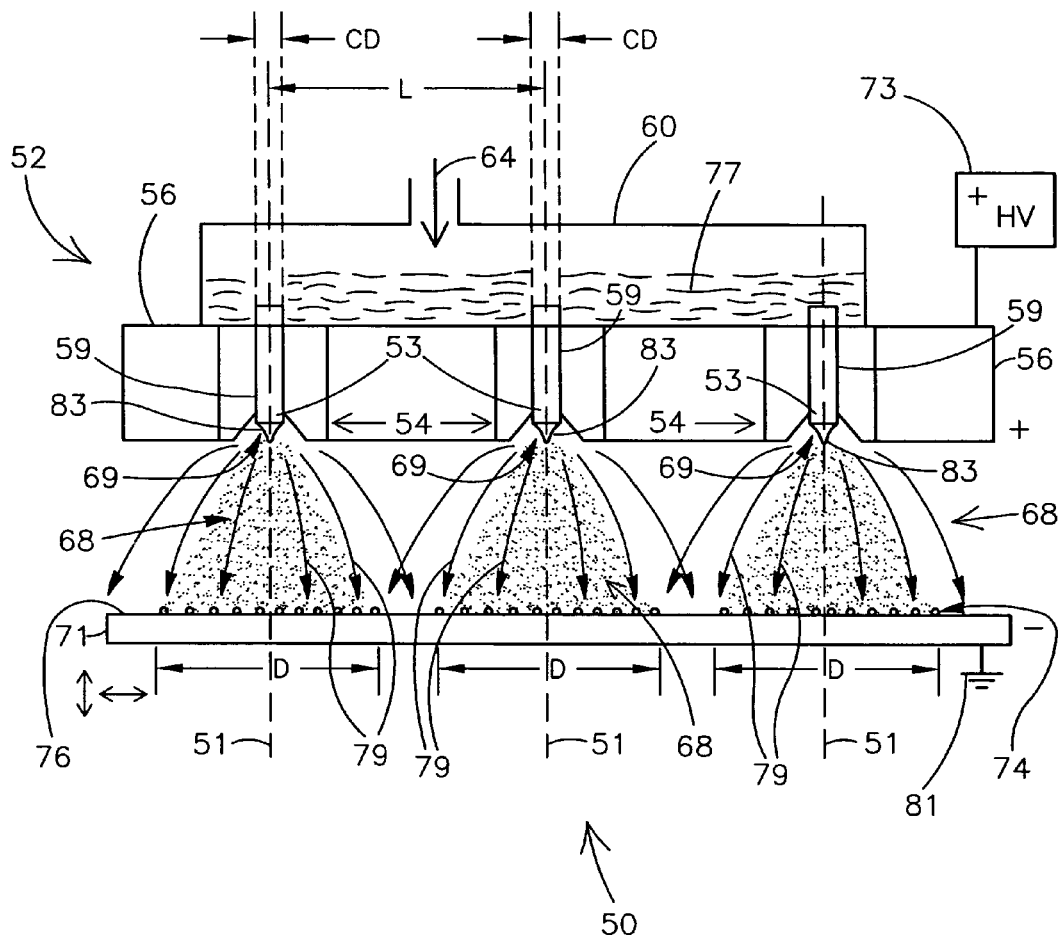
FIG. 2 is a general diagrammatical illustration of one embodiment of an electrospraying dispensing device including multiple nozzle structures for use in a particle generator system shown generally in FIG. 1.

FIG. 2 shows one illustrative embodiment of an electrospray dispensing device 52 that may be employed in a particle generator system 10 such as shown generally in FIG. 1. The electrospray dispensing device 52 includes multiple nozzle structures 54 for establishing a spray of charged particles 68 from each nozzle structure 54. The electrospray dispensing device 52 includes a source material holding apparatus 60 for providing source material 77 to each of the nozzle structures 54, e.g., simultaneously, for use in establishing the sprays of charged particles 68.

A single electrospray nozzle structure can deliver only a limited feed rate of source material in the establishment of a spray of particle 68 within the envelope of the nozzle structure. This limited feed rate of source material can be increased by using the multiple nozzle structures 54 bundled together in one or more various configurations. For example, the feed rate may be increased by "n" times with "n" nozzle structures. The present invention as described further below, enables the employment of as many as 1,000 nozzle structures, e.g., capillary tubes, within a small area, e.g., seven or ten centimeter diameter. The nozzle structures 54, operate to each provide a separate spray of particles 68, increasing the mass throughput for production of nanoparticles.

Figure 6:
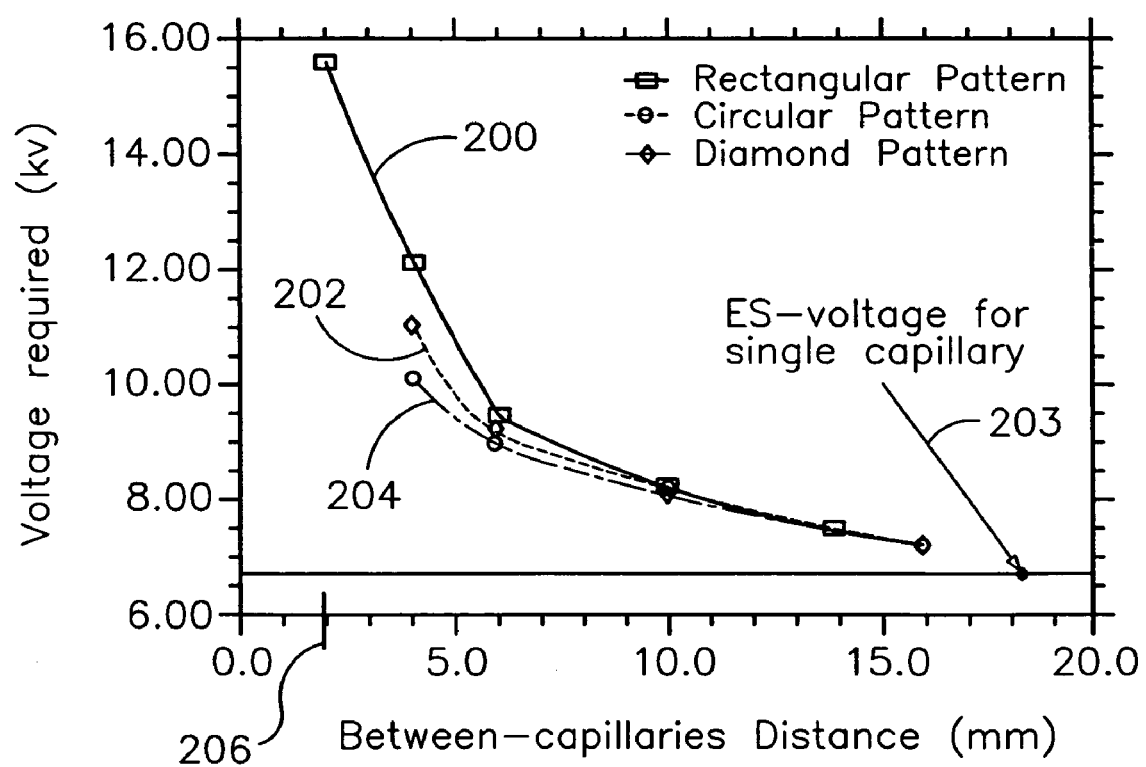
FIG. 6 provides a graph showing the voltage required to form a cone jet in a multiple nozzle structure versus the inter-nozzle distance between such nozzle structures for the multiple nozzle configurations shown generally in FIGS. 3A-3C.

One of various challenges in spraying highly charged nanoparticles from a tightly packed bundle of nozzle structures is to overcome the space charge effect of the nanoparticles from one nozzle structure on other adjacent nozzle structures. As shown in FIG. 6 herein, with respect to various configurations of multiple nozzle structures, generally, the voltage required to form a cone jet mode for a nozzle structure 54 increases with decreasing internozzle distance. However, it is preferable to operate at a lower voltage because with higher voltages arcing between nozzle structures and the second electrode used to form the electric field may become problematic. Therefore, you want a multiple nozzle structure configuration that can have nozzle structures spaced close together with less internozzle distance, but which does not require a high voltage to establish the cone jet.

As shown in FIG. 2, each nozzle structure 54, e.g., a capillary tube 59, defines an opening 53 extending along an axis 51 and terminating at dispensing end 69. The opening 53 has a cross section orthogonal to and centered on the axis 51. As used herein, internozzle distance (L) is defined as the distance between the center axis 51 of nozzle structures 54.

Figure 3A:
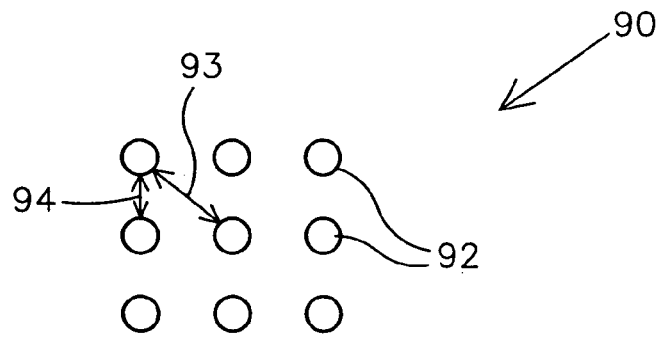
FIGS. 3A-3C show alternate configurations for multiple nozzle structures such as the electrospraying dispensing device shown illustratively in FIG. 2.
Figure 3B:
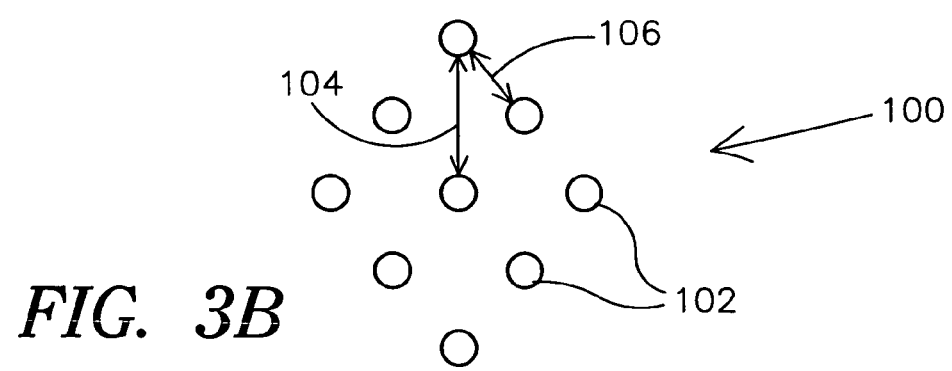
Figure 3C:
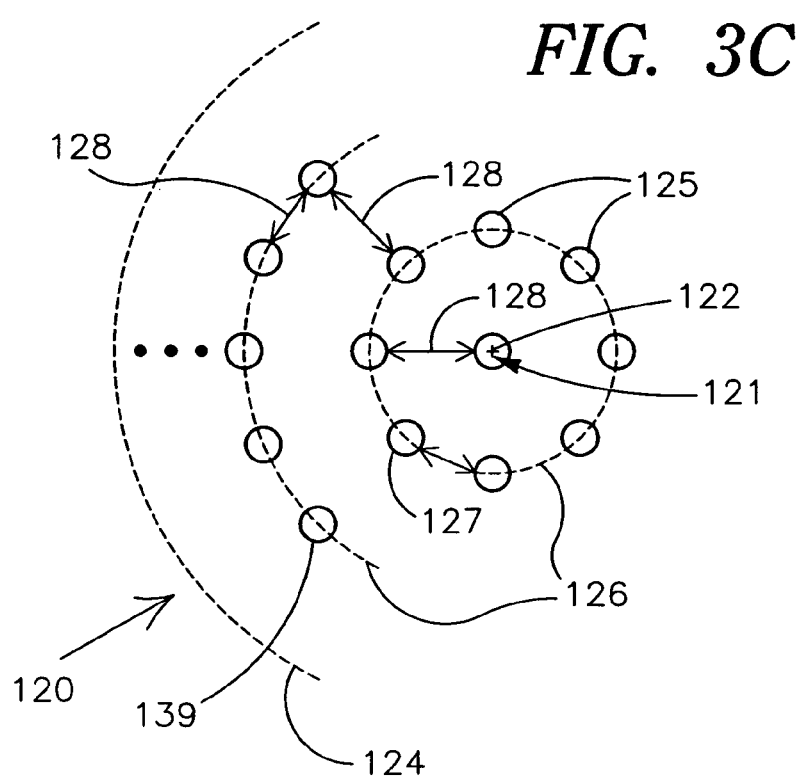

FIG. 6 shows the voltage required as a function of internozzle distance for three nozzle patterns shown in FIGS. 3A-3C. For example, graph line 200 corresponds to the rectangular pattern of nozzle structures generally represented by FIG. 3A, graph line 202 corresponds to a diamond pattern configuration of nozzle structures generally illustrated in FIG. 3B, and graph line 204 corresponds to a circular configuration of nozzle structures generally represented by the illustration in FIG. 3C, and also in FIG. 4.

Generally, in one embodiment, the voltage required to obtain cone jet operation for a single capillary tube 59 as shown by arrow 203 is about 7500 volts. As the internozzle distance (L) decreases, a higher voltage is required to "expel" the highly charged nanoparticles away from the nozzle structure 54 to form the cone jet mode required for spraying nanoparticles. Ultimately, the required voltage reaches the breakdown electric field (approximately 18,000 volts) which defines the closest distance for the internozzle spacing. This is represented by line 206 at approximately 2 millimeters.

The internozzle distance (L) is also affected by the critical dimension (CD) of the opening 53, e.g., the diameter of cross-section of the opening 53 orthogonal to the axis 51, of the nozzle structure 54. For example, as shown in FIG. 2, capillaries 59 are provided along the axis 51 of the nozzle structure 54 with each capillary terminating at a dispensing end 69. The CD for the nozzle structure 54 is the diameter of the opening 53, i.e., the diameter of the cross-section of the opening from which spray is established at the dispensing end 69.

According to the present invention, to avoid the multiple nozzle structures 54 from becoming a single electrode, e.g., arcing from the nozzle structures to the second electrode, a certain internozzle distance (L) must be provided between the nozzle structures 54. Preferably, according to the present invention, the ratio of the internozzle distance (L) to CD, i.e., L/CD, is equal to or greater than 2. In other words, as shown in FIG. 2, preferably, the ratio of the internozzle distance (L) to the diameter of the opening 53 orthogonal to axis 51 is equal to or greater than 2.

Each of the nozzle structures 54 of the electrospray dispensing device 52 provides a charged spray with a high concentration of charged particles. Generally, the concentration of charged particles in the spray is in the range of about $10^5$ particles per cubic centimeter (particles per cc) to about $10^{12}$ particles/cc. Due to the space charge effect, i.e., the effect created by the charge repulsion of charged particles, a spray of substantially dispersed particles having the same polarity charge is provided with the particles distributed substantially uniformly across the spray area (D) as shown in FIG. 2.

As used herein, the term substantially dispersed particles refers to uniformly and/or nonuniformly sized particles separated by an applied repulsive electrostatic force. Thus, the electrospray process is a consistent and reproducible transfer process. Further, because the charged particles of the spray repel one another, agglomeration of the particles is avoided. This results in a more uniform particle size.

Generally, according to the configuration as shown at FIG. 2, the charge is applied by concentration of charge on the spray of particles through evaporation of solution including the material, e.g., active ingredient, in an established electrical field 79. In other words, for example, the source material 77 may be a suspension of active ingredients or a solution including dissolved active ingredients. The suspension or solution is then dispensed from the electrospray dispensing device 52, e.g., active ingredient of microdroplets are dispensed. In other words, the liquid sprayed generally evaporates to concentrate a charge of a liquid portion thereof on the particles, e.g., active ingredient particles, in the fluid composition or suspension being sprayed. This results in the spray of charged particles 68 as described further below.

FIG. 2 generally shows a diagrammatical illustration of the operation of the electrospray dispensing device 52 for establishing charge sprays 68 from each of the nozzle structures 54. Each of the nozzle structures 54 receives a flow of fluid composition from the material source holding apparatus 60. For example, the material source holding apparatus 60 may include a fluid composition 77 suspending drug active ingredients or having active ingredients dissolved therein.

Generally, a conductive material 56, e.g., a conductive plate, positions each of the nozzle structures 54 in a particular configuration. The conductive material 56 is adapted to be connected to a high voltage source 173. Each of the nozzle structures 54 includes a conductive structure, e.g., a capillary tube 59 as illustratively shown in FIG. 2, defining an orifice, e.g., an opening 53 (e.g., a capillary tube opening or an orifice defined in a flooding type chamber, etc.) for receiving a flow of fluid composition 77 therein.

Although various configurations for the source material holding apparatus 60 may be used according to the present invention, preferably a single holding apparatus is used to feed fluid composition 77 to all of the nozzle structures 54. However, one will recognize that any number of different and separate holding apparatus may be used or hold various different fluid compositions and provide different compositions to different nozzle structures 54.

Preferably, the fluid composition 77 may be pushed or pulled through the opening 53 and provided at dispensing end 69 of the nozzle structure 54, e.g., pushed by a pump. Preferably, a compressed gas source represented generally by arrow 64, e.g., an inert source that is non-reactive with the fluid composition 77, is provided to compress the fluid composition 77 and force fluid to flow through openings 53 of the nozzle structures 54. Although preferably, a compressed gas source 64 is used to provide such fluid composition flow, other methods of providing such flow may also be used. For example, a plate above the fluid composition 77 having a force, e.g., pneumatic force, applied thereto may be used, or syringe pumps for each nozzle structure may be used.

The nozzle structures 54 positioned by and electrically coupled to the conductive structure 56 function as a first electrode of the electrospray dispensing device 52 with the dispensing ends 69 of each nozzle structure being positioned for dispensing charged microdroplets toward target 71, or a surface 76 thereof. In the exemplary embodiment of FIG. 2, to set up the electric field 79, the target 71 functions as a second electrode structure, e.g., a grounded target 71. An electrical potential difference is applied between the first electrode conductive structure 56 and the second electrode or grounded target structure 71 that is electrically isolated from the first electrode. One skilled in the art will recognize that the electrodes may be formed using one or more conductive elements and such electrodes may take one of various different configurations.

Generally, in operation, a flow of the fluid composition 77 is provided through the openings 53 of the nozzle structures 54, e.g., pushed and/or pulled through the openings 53. A meniscus is formed at the dispensing end 69 where the opening 53 has a diameter in the preferred range of about 6 microns to about 2 millimeters. A potential difference is applied to establish a nonuniform field 79 between the first electrode conductive structure 56 electrically coupled to the nozzle structures 54 and the second electrode target structure 71 connected to ground 81. For example, a high positive voltage may be applied to the first electrode conductive structure 56 with the second electrode target structure 71 being grounded. Further, for example, a voltage difference that provides an electric field intensity of greater than 4 kV/cm is preferably used.

As used herein, nonuniform electric field refers to an electric field created by an electrical potential difference between two electrodes. The nonuniform electric field includes at least some electric field lines that are more locally concentrated at one electrode relative to the other electrode, e.g., more concentrated at the dispensing end 69 relative to the second electrode or a grounded target surface 71. In other words, for example, at least some of the field lines are off axis relative to the longitudinal axis 51 through the center of the opening 53. Further, for example, the target grounded electrode is positioned forward of dispensing end 69 and is of a size and/or includes at least a portion that is located at a position away from the longitudinal axis 51. In various embodiments, the second electrode may be one or more ring electrodes, plate electrodes, grounded target surfaces, etc.

In a case where the fluid composition includes an active ingredient, the fluid composition 77 is flowed through the opening 53 of the nozzle structures 54. Generally, the fluid composition 77 provided to the opening 53 has an electrical conductivity. As the fluid composition 77 progresses through the opening or orifice 53, the potential difference between the first and second electrodes which creates the electric field therebetween strips the liquid of one polarity of charge, i.e., the negative charge is stripped when a high positive voltage is applied to the electrode 56, leaving a positively charged microdroplet to be dispensed from the dispensing end 69. For example, the meniscus at the dispensing end 69 may form a cone jet for dispensing a spray of microdroplets including the active ingredients when forces of a nonuniform field 79 balance the surface tension of the meniscus. The spray of microdroplets further become more positive in a nonuniform electric field 79.

As the microdroplets evaporate, the charge of the microdroplets concentrate on the active ingredients resulting in a spray of charged particles. The amount of charge on the microdroplet, and thus the amount of charge on a particle after evaporation, is based at least upon the conductivity of the fluid composition used to spray the microdroplet, the surface tension of the fluid composition, the dielectric constant of the fluid composition, and the feed flow rate thereof. Generally, the electric charge concentrated on a particular particle is in the range of about 80% to about 95% of a maximum charge that can be held by the microdroplets, without the microdroplet being shattered or torn apart, i.e., in the range of about 80% to about 95% of the Rayleigh charge limit. At 100%, the surface tension of the microdroplet is overcome by the electric forces causing droplet disintegration. The nonuniform electric field also provides for containment of particles and/or direction for the particles which would otherwise proceed in random directions due to the space charge effect.

One skilled in the art will recognize that the voltages applied may be reversed. For example, the first electrode may be grounded with a high positive voltage applied to the second electrode. In such a case, the particles would have a negative charge concentrated thereon. Further, any other applied voltage configuration providing a nonuniform electric field to establish the charged spray of particles may be used.

The nonuniform electric field can be provided by various configurations. For example, the second electrode may be any conductive material grounded and positioned to establish the formation of a spray 68 from the dispensing ends 69 of the nozzle structures 54, e.g., the second electrode may be a grounded ring electrode, a grounded target surface holding excipient material, a container grounded for use as an inhalation device, etc. The second electrode may also be located at various positions, such as just forward of the nozzle structures 54, or located farther away from the nozzle structures 54 and closer to target surface 76.

The strength of the field may be adjusted by adjustment of the distance between the first and second electrodes. Different field strengths will result in relatively different areas D upon which particle spray is provided, at least in part due to the space charge effect of the sprays of particles 68. One skilled in the art will recognize that one or more components of the dispensing device 52 may be moved relative to the others, e.g., the target surface relative to the nozzle structures 54 or vice versa, to facilitate adjustment of field strength.

The fluid composition 77 from the holding apparatus 60 is provided to the nozzle structures 54, when operable, under control of, preferably, compressed gas source 64. As described above, the flow may also be controlled with use of a liquid pump (e.g., a syringe pump, a gravity feed pump, a pressure regulated liquid reservoir, etc.), a mass flow controller, or any other flow control devices suitable for feeding source material, e.g., fluid composition 77, to the multiple nozzle structures 54 as would be known to one skilled in the art.

The flow of fluid composition is atomized into microdroplets by the dispensing device 52. Atomization may be provided by any known technique for producing microdroplets, which microdroplets preferably have a nominal diameter of about 10 nanometers or greater, more preferably about 20 nanometers to about 10 micrometers, and even more preferably about 30 nanometers to about 1 micrometer. Preferably, electrostatic atomization is used. However, other atomization devices (e.g., pressure regulated atomizers, ultrasonic nebulizers, hydraulic nozzles, etc.) may provide adequate atomization. As described previously herein, microdroplets having nominal diameters in the range of about 10 nanometers to about 2 microns can be produced by electrospray. Various factors as described in such references affect the produced droplet size. For example, capillary size, liquid feed rate, the dispensing device, surrounding gas properties, etc. One skilled in the art will recognize that such factors and others may be modified to produce microdroplets of desired sizes.

By applying different electrical potential differences between the multiple nozzle structures 54, e.g., capillary tube electrodes 59, and the second electrode target 71, different operating modes can be established. For example, a high positive voltage 73 applied to the capillary tube electrodes via the conductive structure 56 with the grounding of the second electrode target 71 provides sprays 68 with a relatively high positive charge. The second electrode 71 in such a case may be provided to ground 81 or may have a negative voltage connected thereto. For example, the voltage applied is limited by the maximum electric field intensity permitted in the medium in which the field is created. For example, arcing will occur in air at an electrical field intensity greater than about 30 kV/cm. However, the allowed electric field intensity can be increased with use of a sheath gas about the nozzle structures, such as $CO_2$, $SF_6$, etc.

With relatively large potential differences being applied, as described in the above-cited papers, pulsating modes or cone jet modes of operation are achieved. In a cone jet mode of operation, a cone shaped liquid meniscus is formed at the dispensing end 69, whereas in the pulsating mode, the shape of a liquid meniscus alternates between a cone shape and a round shape. On the other hand, with relatively low electrical potential differences applied between the capillary tube electrode 59 and the second electrode 71, dripping from the dispensing tip occurs. According to the present invention, a spray from a cone jet 83 formed at the orifice or opening 53 of the capillary tube 59 is preferred.

Although various configurations, as described further below, for the electrospray dispensing device may be suitable, the dispensing device 52 preferably includes capillary tubes 59 made of a suitable material, such as, for example, platinum, silica, etc. for providing the spray 68 from each of the nozzle structures 54, e.g., the capillary tube 59 thereof. For example, the capillary tube may have an outer diameter in the preferred range of about 6 micrometers to about 2.5 millimeters and an inner diameter in the preferred range of about 6 micrometers to about 2 millimeters.

Further, the dispensing device 52 may include a casing about each capillary tube, e.g., a concentric tube, or about the dispensing device 52, e.g., a housing surrounding the spraying portion of the device 52, which may be used to provide a sheath of gas, e.g., $CO_2$, $SF_6$, etc., around the capillary tubes 59 to increase the electrostatic breakdown voltage for the capillary tubes, e.g., to prevent corona discharge. The use of such a sheath of gas is particularly beneficial when the spray is created using the high surface tension liquid, e.g., deionized water.

Several detailed configurations for the nozzle structures 54 are described in further detail below. Preferably, according to the present invention, the configurations of multiple nozzle structures 54 provide sprays of particles from all of the nozzle structures such that particles are delivered at a rate in the range of about 2 grams/minute to about 50 grams/minute. Such a rate provides a desirable quantity of particles, such as drug active ingredient particles, to be used in one or more various applications or later processing.

The multiple nozzle structures 54 may be provided in one or more various different configurations. For example, several illustrative embodiments of such configurations are shown in FIGS. 3-5.

A rectangular pattern configuration 90 is shown in FIG. 3A. The rectangular pattern configuration 90 comprises nozzle structures 92 aligned in an array. The internozzle distances 93 and 94 are generally different between such nozzle structures 92.

An alternate diamond pattern nozzle structure configuration 100 is shown in FIG. 3B. The diamond pattern configuration 100 includes nozzle structures 102 provided in a diamond shape have internozzle distances 104 and 106. Such internozzle distances 104 and 106 are not equal between such nozzle structures 102.

FIG. 3C shows a circular pattern configuration of nozzle structures 125. The circular configuration of nozzle structures 125 include a center nozzle structure 122 positioned along an axis 121, an outer ring 124 of multiple nozzle structures 125, and one or more inner rings 126 of multiple nozzle structures 125 that lie between the center nozzle structure 122 and the outer ring 124. The outer ring 124 of multiple nozzle structures and the one or more inner rings 126 of multiple nozzle structures are concentric about the center nozzle structure 122.

The nozzle structures 125 in the circular configuration 120 are separated from each other by an internozzle distance 128. Preferably according to the present invention, each of the nozzle structures 125 of the one or more inner rings are at a substantially equal internozzle distance (L) from adjacent nozzle structures 125.

As used herein, substantially equal internozzle distance refers to a distance that is generally equal between such nozzle structures such that the space charge effect of the sprayed particles established at one nozzle structure has an essentially equivalent effect on adjacent nozzle structures. For example, the effect of the spray of particles established at the center nozzle structure 122 has an equivalent effect on an adjacent nozzle structure 127 of the adjacent inner ring 126 as a spray of particles established from a nozzle structure 139 in an adjacent inner ring 126. In such a manner, the substantially equal internozzle distance (L) provides for substantially equivalent space charge effects on each of the nozzle structures 125 of the inner rings 126 and the center nozzle structure 122. Obviously, somewhat different space charge effect will affect the nozzle structures 125 of the outer ring 124 as those nozzle structures 125 in the outer ring 124 do not have nozzle structures adjacent to both sides thereof.

Preferably, the present invention is employed in this circular configuration 120 with substantially equal internozzle distance (L) represented by reference numeral 128. This is as opposed to the employment of the rectangular and/or diamond configurations of FIGS. 3A and 3B, wherein the distances between nozzle structures are not substantially equal.

Figure 4:
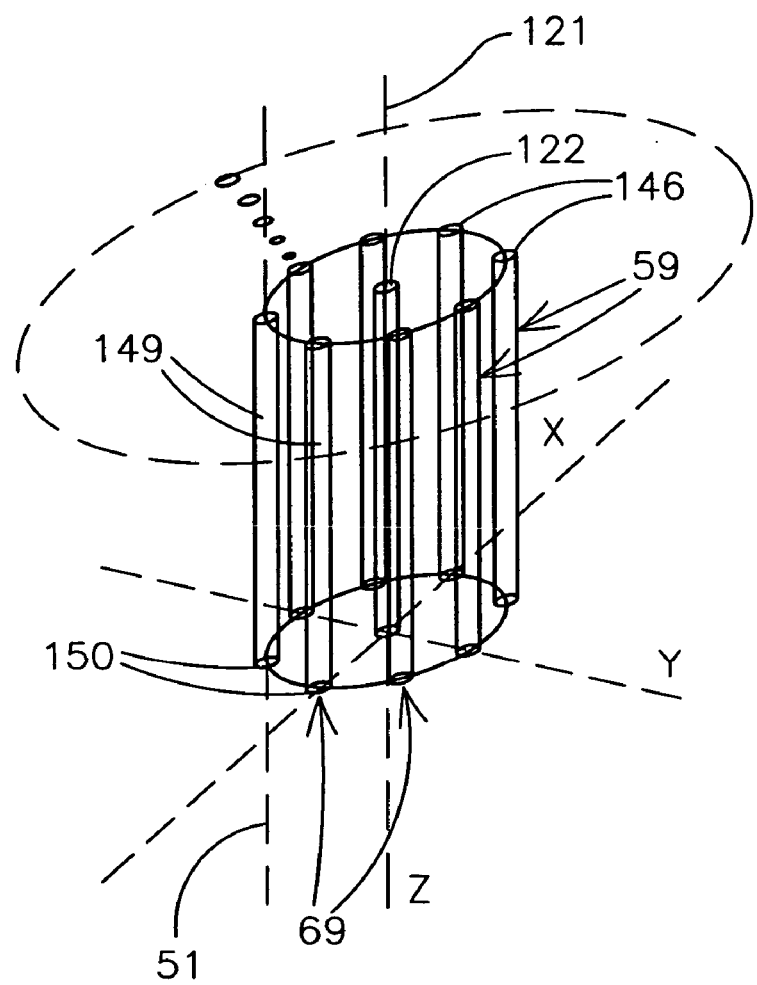
FIG. 4 shows one illustrative embodiment of a circular configuration of multiple nozzle structures shown generally in FIG. 3C.

Preferably, as shown in FIG. 4, the dispensing ends 69 of the nozzle structures generally fall in a single X and Y plane. Further, in at least one particular illustrative embodiment, each of the nozzle structures 54 include the capillary tubes 59 having a body portion 149 terminating at a capillary tube tip 150. In other words, preferably, the capillary tube tips are all provided in a single X and Y plane. Further, as shown in FIG. 4, each of the capillary tubes 59 is generally located along a center axis 51 of the nozzle structure 54 (see FIG. 2) which is generally parallel to the z axis. In other words, the capillary tubes 59 are positioned with the tips 150 thereof lying in an XY plane, and further are positioned in a circular configuration and aligned along the Z axis.

As shown in FIG. 6, the circular pattern configuration 120 requires the least voltage to form the cone jet mode for the nozzle structure 54. As such, it is apparent that the circular configuration 120 allows the most compact bundle arrangement for the capillaries without breakdown in the electric field. With such a circular pattern configuration 120, it is possible to put 1,000 nozzles within a 7 to 10 centimeter diameter disk that is a typical area to operate a single spray nozzle. Therefore, such a density of nozzle structures may increase the mass throughput by a factor of over 1,000. The diagram as shown in FIG. 3C represents the use of multiple rings and clearly is not shown to scale as many additional nozzle structures 125 and rings may be provided into this circular configuration 120. Likewise, the configurations of FIGS. 3A-3B are also not to scale and can accommodate many more nozzle structures in such configurations.

Figure 5A:
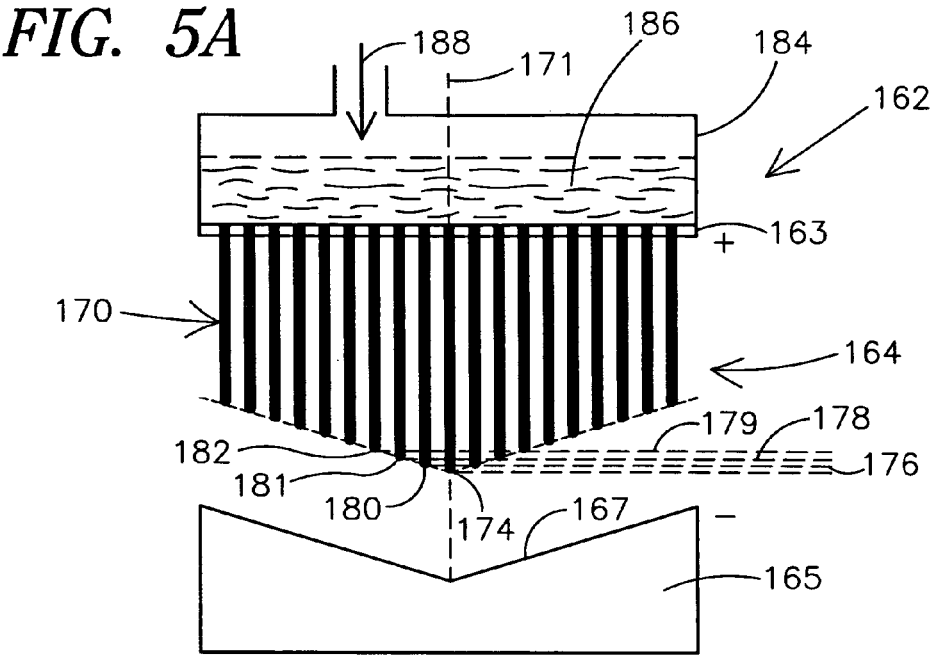
FIGS. 5A-5B show an illustrative side view diagram of a conical configuration of multiple nozzle structures and an illustrative bottom view of the conical configuration according to the present invention.
Figure 5B:
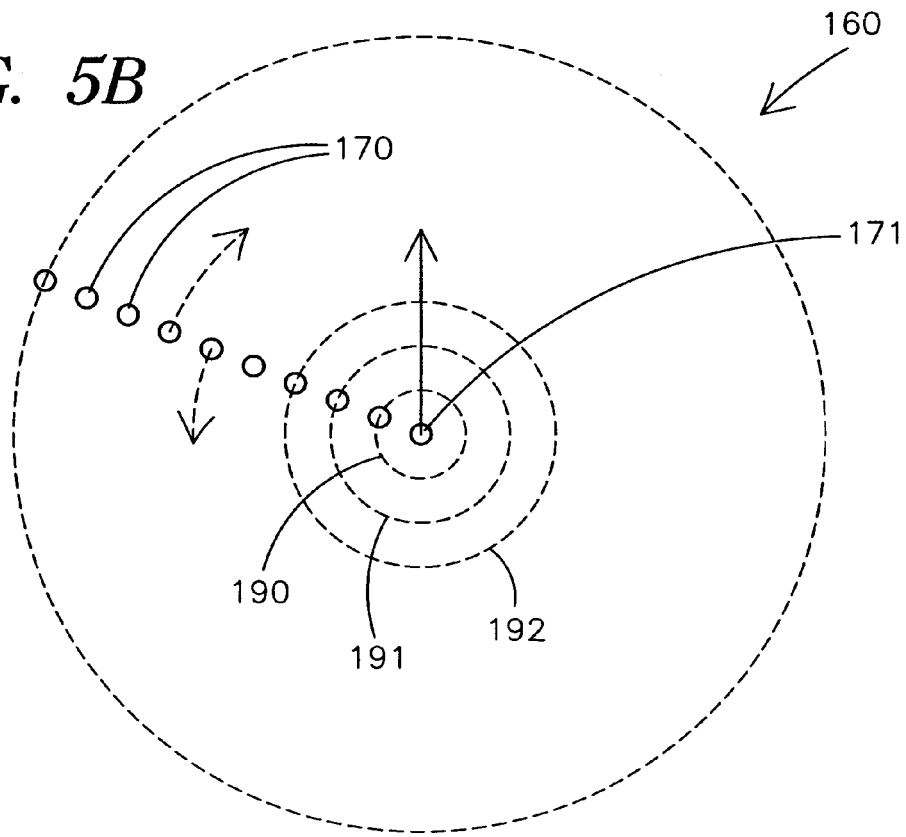

FIGS. 5A-5B show a side view and a bottom view of an alternate conical configuration 160 for the nozzle structures. As shown in FIG. 5A, an electrospray dispensing device 162 includes a conductive plate 163, e.g., first electrode, that positions and is electrically coupled to a plurality of capillaries 170, e.g., first electrode. The plurality of capillaries 170 are fed a flow of fluid composition 186 held in fluid composition holding apparatus 184 under control of compressed gas source 188 and a negatively held target 165 provides the nonuniform field for providing a spray of particles from each of the capillaries 170.

In the conical configuration 164 of the capillary tubes 170, different inner rings of capillary tubes 170 are terminated at different planes orthogonal to axis 171 through center capillary tube 174. In other words, as shown in FIGS. 5A-5B, first inner ring 190 of capillaries 170 have capillary tips 180 that terminate at a plane 176 orthogonal to axis 171. Likewise, inner ring 191 of capillaries 170 terminate at tips 181 and in plane 178 orthogonal to axis 171, and likewise, inner ring 192 of capillaries 170 have tips 182 thereof that terminate in plane 179 orthogonal to axis 171. Likewise, one or more additional inner and outer multiple nozzle structure rings terminate at other planes orthogonal to axis 171 to form the conical configuration 164. The center capillary has a tip 174 at the tip of the cone as shown in FIG. 5A.

Although the present invention is described with regard to preferred configurations of nozzle structures, one skilled in the art will recognize that from the description herein, various other configurations may also be possible, e.g., pentagon shaped, hexagon shaped, etc. Further, clearly, the present invention is not limited to any particle type of nozzle structure employed in such configurations as various suitable nozzle structures may be employed. For example, various nozzle structures have been previously described generally herein and others are described with respect to FIGS. 7-12. Any nozzle structure suitable to provide a spray of particles according to the principles described herein may be used, e.g., a slit that may provide various cone jets (e.g., with or without posts as described below), nozzle structures having portions thereof that are integral with portions of other nozzle structures, etc.

For example, as previously described herein, capillary tubes made of a suitable material, such as, for example, platinum, silicon, etc., may be used for providing sprays of particles as described herein. Preferably, such capillary tubes are tapered at the tips thereof so as to concentrate the electric field at the tip of each capillary.

Figure 7:
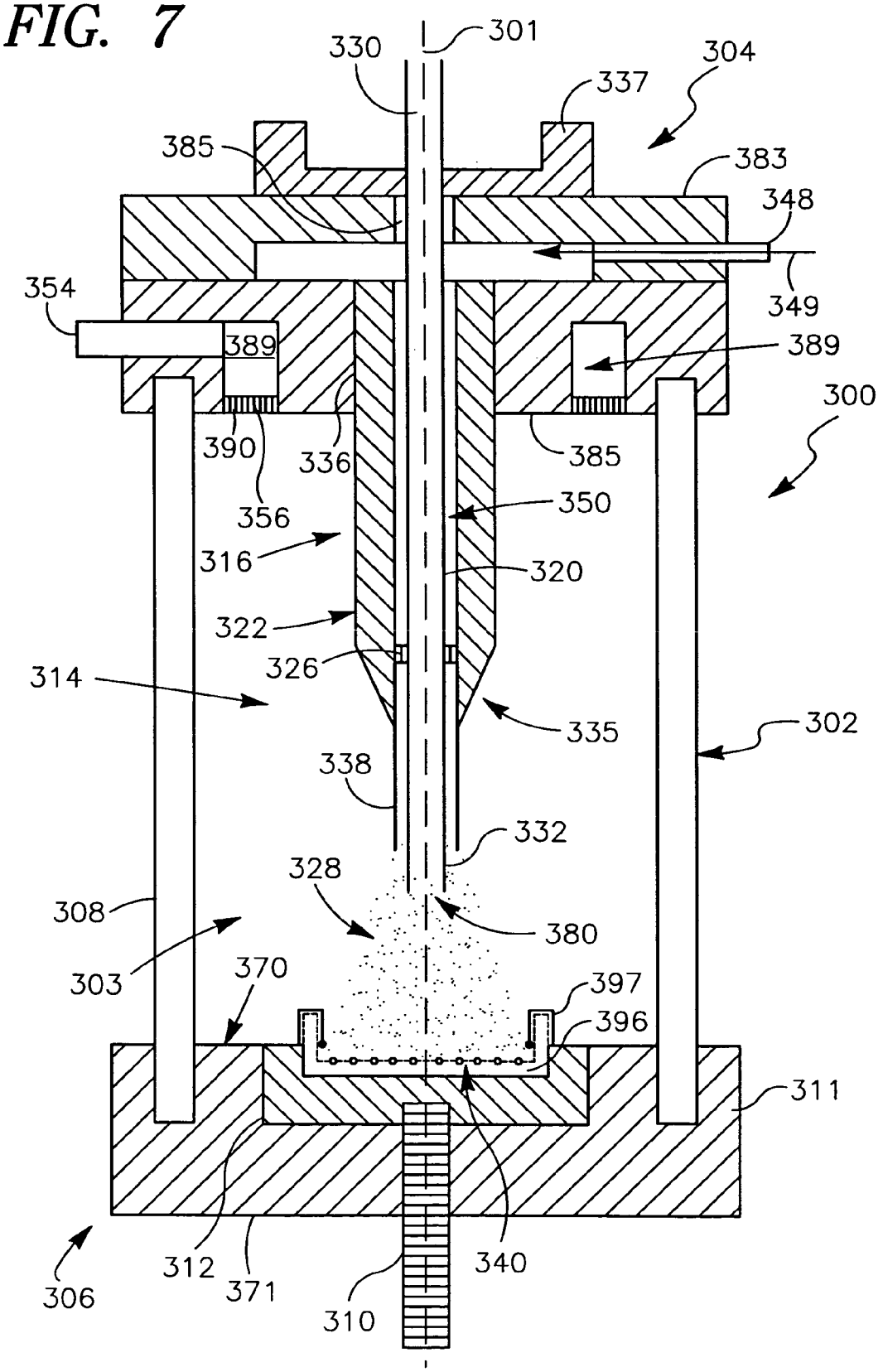
FIG. 7 is one illustrative exemplary embodiment of a nozzle structure that may be employed in the illustrative multiple nozzle electrospray dispensing device of FIG. 2.
Figure 8:
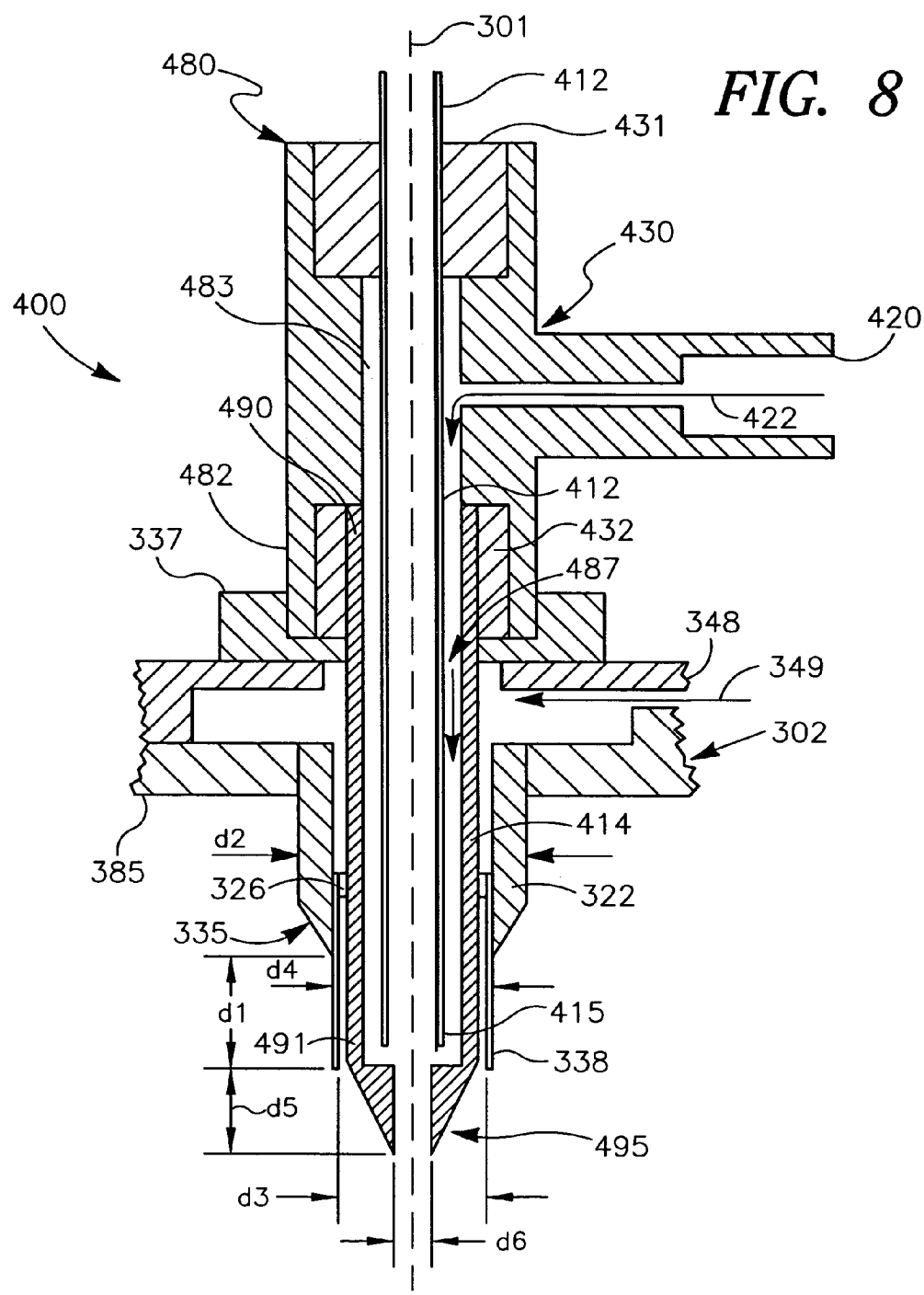
FIG. 8 is an alternate embodiment of another nozzle structure using a dual stream technique that may be employed in the multiple nozzle electrospray dispensing device of FIG. 2.

Several illustrative examples utilizing capillary tubes are described herein with reference to FIGS. 7 and 8. For example, FIG. 7 is a more detailed diagram of one configuration of a portion 300 that may be at least in part, e.g., the dispensing portion 314, employed as a part of a nozzle structure 54 of the electrospray dispensing device 52 shown generally in FIG. 2.

As shown in FIG. 7, spray 328 is sprayed into a chamber 303 defined by a housing 302 having an axis 301 therethrough. The housing 302 includes a first end 304 and a second end 306 connected therebetween with a cylindrical wall about axis 301. Preferably, the housing 302 is a vacuum chamber which can be evacuated. The housing 302 is generally formed of insulative materials. For example, the cylindrical wall enclosure 308 is preferably a plexiglass cylindrical wall for visibility while the first and second ends 304, 306 may be formed of various insulative materials. First end 304 may also be formed of conductive portions, e.g., conductive material 56, to facilitate application of voltages or ground to the capillary tube 320.

The second end 306 of the housing 302 includes an end element 311 connected to the cylindrical walls 308. Positioned relative to an upper surface 370 of the end element 311 is a target platform 312, e.g., part of second electrode, upon which target material, e.g., excipient material, can be positioned. For example, a tube, dish, or any other structure may be positioned on the platform 312. Further, a rotatable micrometer adjustment mechanism 310 is provided through a lower surface 371 of the end element 311 for contact with platform 312 such that the height of the platform 312 can be varied, e.g., the distance between the target and the dispensing tip 380 can be adjusted. The platform 312 is formed of a conductive material, e.g., stainless steel, and may function as the second electrode for establishing spray 328 from the dispensing tip 380.

The first end 304 of the housing 302 includes a distributor head 316 extending therethrough having an axis that is coincident with axis 301 for use in establishing the spray 328 in the chamber 303 in combination with conductive platform 312. The distributor head 316 includes a capillary tube 320 having an axis therethrough coincident with axis 301. The capillary tube 320 includes a first end 330 sealingly positioned in aperture 385 of the first end 330 by conductive sealing element 337 at the upper surface 383 of the first end 304. The capillary tube 320 further includes a second end 332 positioned for dispensing spray 328 as desired. The capillary tube 320 may be made of any suitable material, such as, for example, platinum, silica, stainless steel, etc. and may be of any suitable size. For example, the capillary tube may preferably have an outer diameter in the range of about 8 μm to about 2.5 mm, and an inner diameter in the preferred range of about 6 μm to about 2 mm. More preferably, the inner diameter of the capillary tube is in the range of about 10 μm to about 200 μm.

Further, the distributor head 316 includes a nozzle portion or casing 322 which as illustrated in FIG. 7 is an elongate substantially cylindrical metal casing concentric with the capillary tube 320. However, the casing 322 can be conductive or nonconductive. Further, the casing 322 can take any configuration or shape which allows for the flow of a sheath gas about the capillary tube 320. Together, in this particular embodiment, the capillary tube 320 and the casing 322 form the capillary tube electrode of the distributor head 316 for use in providing the spray 328 into the chamber in conjunction with the conductive platform 312. The casing or nozzle portion 322 includes a first end portion 336 which tapers at section 335 thereof to a narrower second end portion 338. The second end portion 338 extends from the tapered section 335 and is concentric with the second end 332 of the capillary tube 320. The narrow end of the tapered section 335 extends a preferable distance of about 5 mm to about 5 cm from the lower surface 385 of the first end 304. The outer diameter of the second end portion 338 is preferably in the range of about 2 mm to about 5 mm and the inner diameter of the second end portion 338 is preferably in the range of about 0.1 cm to about 0.2 cm. The second end 332 of the capillary tube 320 extends beyond the second end portion of the metal casing or nozzle portion 322 towards the target cells 340 by a distance of preferably about 2 mm to about 5 mm. The nozzle portion 322 is formed of any suitable metal or nonconductive material such as stainless steel, brass, alumina, or any other suitable conductive or nonconductive material. The nozzle portion 322 is spaced from the capillary tube 320 by spacers 326 or other spacing structures. For example, a metal casing 322 may be deformed at particular portions, such as pin points or depressions, to create a neck for centering the capillary tube 320 therein.

The capillary tube electrode may take one of many configurations. However, of primary importance is that the capillary tube electrode provide an electrode for creating the nonuniform electric field and, optionally, provide a gas sheath about the capillary tube to avoid corona discharge if spraying high surface tension liquids, e.g., deionized water. For example, in an electrospraying apparatus wherein the spray is established in a chamber, the capillary tube electrode may just include a capillary tube itself, as opposed to requiring a casing such as metal casing 322 to provide an annular space for flow of the sheath gas. In such a configuration, e.g., a multiple nozzle configuration, that uses many capillary tubes, the chamber may be flooded with the gas for preventing corona discharge. Further, when spraying liquids other than high surface tension liquids, the gas sheath may not be required.

A gas inlet 348 is provided in the first end 304 of housing 302 to allow for input of a stream of electro-negative gases, e.g., $CO_2$, $SF_6$, etc., to form a gas sheath about the capillary tube 320. The inlet is configured for directing a stream of an electro-negative gas in an aperture 350 between the concentric capillary tube 320 and the nozzle portion 322. This gas sheath allows the applied voltage to be raised to higher levels without corona discharge, e.g., the electrostatic breakdown voltage for the capillary tube electrode is increased. The entire portion of end 304 or portions thereof may be formed of conductive materials to facilitate application of a voltage or ground to the capillary tube electrode. For example, sealing elements 337 may be nonconductive, but is preferably conductive to facilitate application of a voltage or ground to capillary tube 320.

The first end 304 further includes an exit port 354 for gases to exit the chamber 303. For example, the exit port 354 may open into an annular chamber 389 defined in the first end 304 having a bottom face plate 390 having a series of holes for allowing flow from the chamber 303 out through the exit port 354. A vacuum pump may be connected to the exit port 354 for evacuating the chamber 303 to a low pressure. For example, preferably, the pressure in the chamber is in the range of about 1 atmosphere to about 0.1 atmosphere. Further, instead of or in addition to providing the gas sheath between the capillary tube 320 and the nozzle portion 322, the chamber 303 may be flooded with a gas through the exit port 354 to increase the electrostatic breakdown voltage for the capillary tube electrode.

In one embodiment, the chamber 303 is flooded with the gas through the exit port 354 and then a flow in the preferred range of about 5 cc/min to about 200 cc/min is continued through the exit port 354. Any port to the chamber 303 may be used for exit of gas from the flooded chamber, e.g., such as a port that is available for sensing pressure (not shown) in the chamber. When the chamber 303 is flooded, the gas sheath between the capillary tube 320 and the nozzle portion 322 may not be necessary. As such, flooding of the chamber is an alternative to the use of such a gas sheath between the capillary tube 320 and the nozzle portion 322.

To establish the spray 328 in the chamber 303, for example, a suspension is provided and received in the first end 330 of the capillary tube 320. Preferably, the flow rate of the suspension may be in the range of about 0.01 μl/min to about 5 μl/min. Preferably, a relatively high voltage, for example, in the range of about 2000 volts to about 6000 volts, may be applied to the platform 312 relative to the capillary tube 320 which is electrically grounded (or vice versa) to establish the potential difference between the first and second electrode of the spraying apparatus. In this particular illustrative configuration, capillary tube 320, metal casing 322, and sealing element 337 are conductive. Spray 328 is established forward of the dispensing tip 380 of the second end 332 of the capillary tube 320 per a mode of operation as previously described. The potential difference between the electrodes establishes an electric field therebetween causing the formation of a smaller filament at the meniscus formed at the dispensing tip 380 while attracting the suspension downward toward the target.

FIG. 8 is a more detailed diagram of an alternate capillary electrode configuration 400 for the distributor head 316 of FIG. 7. Like reference numbers are used in FIG. 8 for corresponding like elements of FIG. 7 to simplify description of the alternate capillary configuration 400. Generally, the alternate capillary electrode configuration 400 is substituted for or replaces the single capillary tube 320 of the structure shown in FIG. 7.

The capillary electrode configuration 400 includes a first capillary tube 412 having an axis coincident with axis 301 for receiving the suspension or fluid composition being sprayed. Further, a second capillary tube 414 is concentric with the first capillary tube 412. An annular space 487 between the inner and outer capillaries 412, 414 is used to direct a stream of a second fluid composition to the dispensing tip 495 for use in establishing the spray forward thereof. For example, an electrolyte solution or a coating or encapsulant material may be provided to the dispensing tip 495 for establishing the spray of microdroplets therefrom. The stream of the second fluid composition is directed in the annular space 487 such that it comes into contact with the suspension, i.e., the first fluid composition, proximate the dispensing tip 495.

In more detail, the housing portion 430 includes an aperture 483 extending from a first end 480 of the housing portion 430 to a second end 482 thereof. An inlet port 420 opens into the aperture 483. The inlet port 420 receives a flow of second fluid composition 422 to be directed in the annular space 487 about the capillary tube 412. The first capillary tube 412 has a first end 413 and a second end 415. The capillary tube 412 is positioned in the aperture 483 of the housing portion 430 of generally T-shaped configuration. The first end 413 of the capillary tube 412 is sealed to housing 430 using conductive element 431 at the first end 480 of the housing portion 430. The capillary tube 412 extends from the second end 482 of the housing portion 430 and with the second capillary tube 414 forms the annular space 487.

The second capillary tube 414 includes a first end 490 and a second end 491. The second capillary tube 414 is positioned so that it is concentric with the first capillary tube 412. The first end 490 of the second capillary tube 412 is coupled to the second end 482 of the housing portion 430 using conductive element 432. Further, the second end 491 of the second capillary tube 414 is held in place relative to the nozzle portion 322 by spacers 326. The second capillary tube 414 extends beyond the first capillary tube 412 a predetermined distance in the direction of the target of preferably about 0.2 mm to about 1 mm. The portion of the second capillary tube 414 at the dispensing tip 495 which extends beyond the first capillary tube is tapered at a 60 degree to 75 degree angle for obtaining stable spray pattern and operation mode, i.e., consistent spraying patterns. Without the taper, intermittent operation may occur. Further, the second capillary tube 414 extends beyond the second end 338 of the nozzle portion 322 a predetermined distance (d5), preferably about 2 mm to about 5 mm. The first capillary tube 412 has preferable diameters like that of capillary tube 320 of FIG. 7. The second capillary tube concentric with the first capillary tube has a preferable outer diameter of about 533.4 µm to about 546.1 µm and a preferable inner diameter of about 393.7 µm to about 431.8 µm. The gap d6 at the tip of the second capillary tube 414 is preferably in the range of about 10 µm to about 80 µm. The other preferred configuration parameters are substantially equivalent to that described with reference to FIG. 7.

In such a configuration, dual streams of liquids are provided for establishing a spray from dispensing tip 495 of the apparatus. Further, a gas sheath may also be provided through inlet port 348 as previously described with reference to FIG. 7. Yet further, the first capillary tube 412 may extend beyond the end of the second capillary tube 414, e.g., the dispensing tip is formed at the end of first capillary tube 412 which is closer to the target than the end of the second capillary tube 414. In other words, the first fluid composition, e.g., the suspension, may contact the second fluid composition before exiting the dispensing tip 495 or the suspension may contact the second fluid composition upon exiting the end of the first capillary tube 412. Further, the second capillary tube may take various other configurations to form the space for providing the second fluid composition to the dispensing tip, e.g., not necessarily a capillary tube structure.

The dual capillary configuration may be used to spray coated particles of active ingredients or create particles having more than one ingredient. For example, active ingredients may be provided by the first fluid composition and a coating material, e.g., a time release polymer, may be provided by the second fluid composition. When sprayed, the coating material encapsulates the active ingredient, at least in part.

Further, the second fluid composition could be an electrolyte solution having a particular conductivity to adjust the charge concentrated on the particles, e.g., a fluid composition that is or may not be compatible with the first fluid composition. The electrical conductivity of such electrolyte liquids is preferably in the range of about 60 $\mu\Omega^{-1}$/cm to about 80,000 $\mu\Omega^{-1}$/cm. The particle size can be controlled with control of the conductivity of the particles. For example, with increased conductivity, particle size is decreased.

Figure 9:
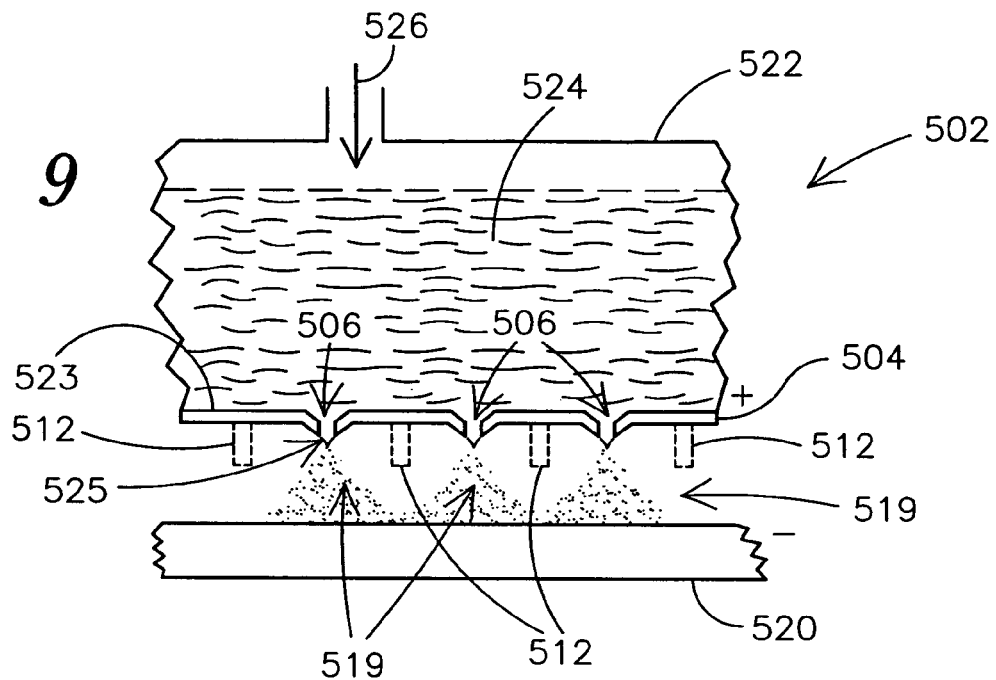
FIG. 9 shows an alternate configuration of providing multiple electrospray nozzle structures according to the present invention that may be employed in the particle generator system shown generally in FIG. 1 according to the present invention.

The nozzle structures may also be provided in one or more of the multiple nozzle structure configurations described herein using an alternate manner of providing the nozzle structures as shown in FIG. 9. A electrospray dispensing device 502 that may be employed in the particle generator system of FIG. 1 includes multiple nozzle structures 506. The multiple nozzle structures 506 are provided, preferably, by a single integral conductive material 504, e.g., a micro-machine plate. The conductive material or micro-machined plate 504 may form a part, e.g., the bottom surface 523, of fluid composition holding apparatus 522 for containing fluid composition 524 and providing a flow of fluid composition 524 to each of the nozzle structures 506. For example, as described previously herein, a compressed gas source 526 may be used to deliver the fluid composition 524 to each orifice or opening 525 of the nozzle structures 506. With a potential difference provided between the conductive material 504, in which the multiple nozzle structures 506 are formed, and the target 520, cone jets 517 (see FIG. 10) are provided at dispensing ends 513 of the multiple nozzle structures 506 to provide the sprays of particles 519.

Figure 10:
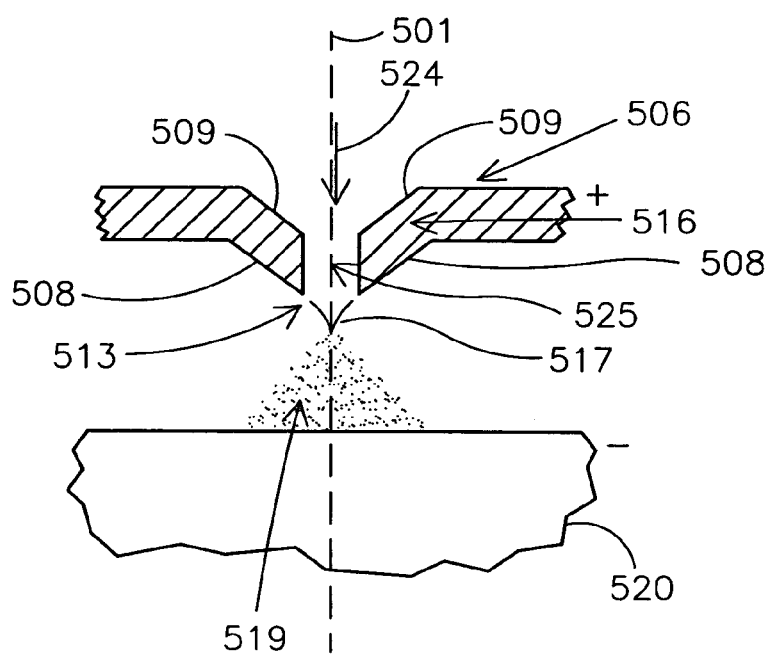
FIG. 10 shows a more detailed illustrative embodiment of a nozzle structure employed in the configuration of FIG. 9.

FIG. 10 shows one of the nozzle structures 506 of FIG. 9 in further detail. The nozzle structure 506 includes a tapered portion 516 that defines the orifice or opening 525. The opening 525 of the nozzle structure 506 extends along the axis 501. The tapered portion 516 includes tapered inner surfaces 509, i.e., inner relative to the fluid composition, to receive fluid composition 524 and provide sufficient flow into opening 525. The tapered portion 516 further includes outer tapered surfaces 508. The outer tapered surfaces 508 and inner tapered surfaces 509 are preferably opposing surfaces having a generally parallel configuration. In other words, such tapers are at the same angle relative to the generally plate like conductive material 504 which lies orthogonal to axis 501. The tapered outer surfaces 508 extend towards the target 520 and terminate at dispensing end 513 at which a cone jet is formed when operating under the applied potential difference.

Figure 11:
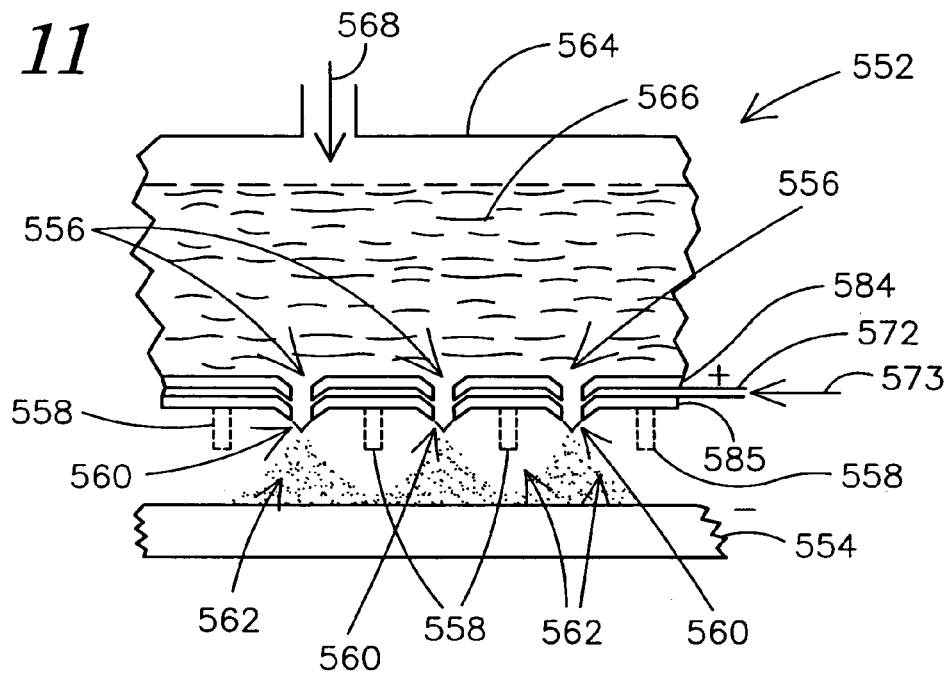
FIG. 11 shows another alternate configuration for providing multiple electrospray nozzle structures that may be employed in the particle generator system shown generally in FIG. 1 according to the present invention.
Figure 12:
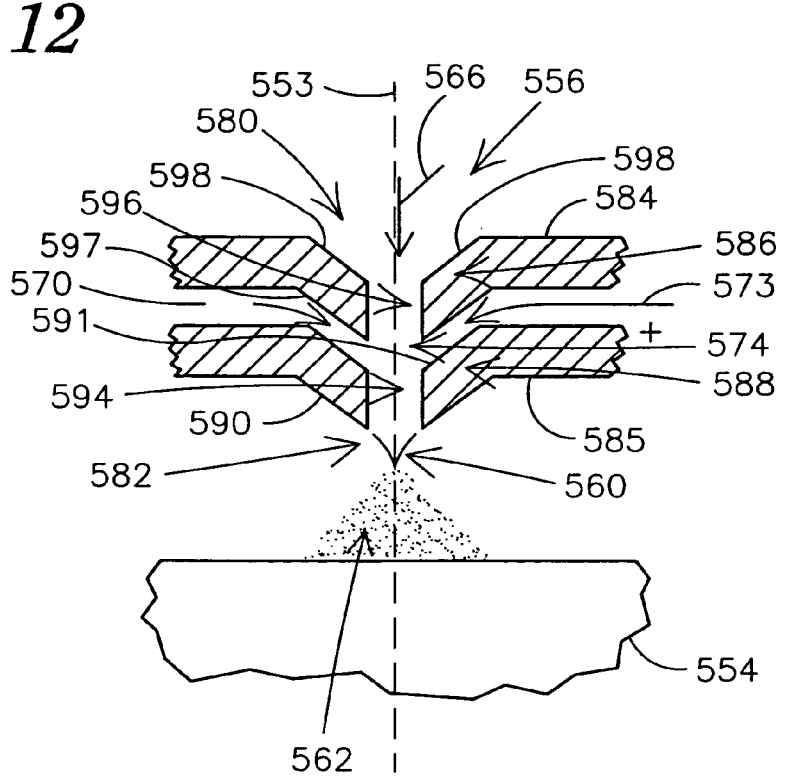
FIG. 12 shows a more detailed illustrative embodiment of a nozzle structure employed in the configuration of FIG. 11.

FIGS. 11 and 12 show a diagrammatic illustration of another alternate embodiment of an electrospray dispensing device 552 that includes multiple nozzle structures 556 in a similar manner to that shown in FIGS. 9-10, but having a dual opening configuration. In such a manner, this apparatus may be used in a manner similar to that described previously with respect to FIG. 8 which shows the use of concentric capillaries.

As shown in FIG. 11, the dispensing device 552 includes generally two conductive plate like structures 584 and 585 acting as the first electrode of the device 552. The conductive plate like structures 584 and 585 are separated to allow for a fluid composition 573 to be provided therebetween from a fluid composition source 572. The plate like structures 584 and 585 are formed to provide the dual opening nozzle structures 556. Each of the nozzle structures 556 form a cone jet 560 upon application of a suitable potential difference between the first electrode, i.e., the conductive plate structures 584 and/or 585 and the target 554. As such, a spray of particles 562 is provided or established at the dispensing ends 582 (see FIG. 12) of each nozzle structure 556.

Once again under application of compressed gas 568, fluid composition 566 held in holding apparatus 564 is provided for flow through each of the nozzle structures 556. The fluid composition 566 may be the same or different than the fluid composition 573. Preferably, the fluid composition 566 is different than the fluid composition 573. For example, as previously described herein, fluid composition 566 may include an active ingredient for medicinal purposes and the fluid composition 573 may include an excipient or a coating material, such as a time release material, e.g., a polymer. With the use of such fluid compositions, coated particles can be sprayed from each nozzle structure 556.

FIG. 12 shows a more detailed drawing of one nozzle structure 556 employed in the dispensing device 552. As shown in FIG. 12, first conductive plate structure 584 provides for the definition of an opening 596 through which first fluid composition 566 is provided. The first conductive plate structure 584 and the second plate structure 585 provide for a space or channel 570 therebetween to receive a second fluid composition 573. The second fluid composition 573 meets the first fluid composition 566 at opening 594 defined by the second conductive plate structure 585. Depending on the configuration defining the openings 594, 596 and channel 570, the two fluid compositions may come into contact with each other in either the channel 570 or the opening 594.

The first conductive plate structure 584 includes a tapered portion 586 that defines the opening 596 along axis 553. The tapered portion 586 includes inner tapered surfaces 598, i.e., relative to fluid composition 566, that receive fluid composition 566, and outer surfaces 597 tapered in a manner, preferably like those of inner surfaces 598. The outer surfaces 597 extend towards the target 554 and terminate at an outlet 574 into channel 570.

Likewise, conductive plate structure 585 includes tapered portion 588 which defines opening 594 along axis 553. The tapered portion 588 includes inner surfaces 591 that receive the second fluid composition 573 and the first fluid composition 566 provided via outlet 574. The tapered portion 588 further includes outer tapered surfaces 590 that terminate at dispensing end 582 such that when a potential difference is applied between the conductive plate structures 585, 588 and the target 554, a cone jet 560 is formed at the dispensing end 582.

It will be recognized that drilling simple holes in conductive plates will not provide for the formation of a cone jet at an orifice thereof. As shown in FIGS. 9-12, to form a cone jet at the dispensing ends of the nozzle structures shown therein, each of the nozzle structures must include a protrusion from a plate like structure. In other words, the tapered portions of the nozzle structure shown in FIGS. 9-12 which provide a protrusion or extension from such plates are required to allow for the formation of a cone jet at the tip of such protruding structures. Such plate like structures may allow for closer spacing of nozzle structures as they can be micro-machined with very tight tolerances.

As previously described herein, the nanoparticles of the sprays established at the dispensing ends of the nozzle structures are generally highly charged which occurs because of an increasingly higher voltage potential applied to the nozzle structure to operate in cone jet mode. Because of the increasingly higher voltage potential, eventually, a corona discharge and voltage breakdown may occur and destroy the cone jet. As shown in FIG. 13, and other embodiments herein, it is possible to use a separation structure, e.g., structure 614 to isolate each nozzle structures from adjacent nozzle structures to reduce the space charge effect caused by the highly charged nanoparticles. This separation structure technique provides one method of allowing the nozzle structures to be highly packed into a small region.

FIG. 13 shows an electrospray dispensing device 600 that employs such isolation techniques. The electrospray dispensing device 600 includes multiple nozzle structures 604 positioned for spraying within a housing 601. Each of the nozzles structures 604 is provided by a capillary tube inserted and electrically coupled to a conductive plate 608 that allows a potential difference to be applied between the capillary tubes 606 and a grounded target 615. Each of the capillary tubes 606 allows for a cone jet 618 to be formed at the dispensing ends 619 thereof. The capillary tubes 606 are provided with a flow of fluid composition 613 held in holding apparatus 612, e.g., provided under control of a compressed gas source 616.

To isolate each of the dispensing ends 619 of each of the nozzle structures 604 from one another, a separation structure or rib separator 614 is provided. This separation structure 614 may be integral with the conductive plate 608 into which capillaries 606 are inserted or may be separated therefrom. Various configurations for the separation structure 614 may be used. For example, as shown in FIG. 13, a separation structures extending from the plate 608 are provided between each of the capillaries 606. One skilled in the art will recognize that any form or size of such separation structure 614 may be used as long as suitable isolation of the dispensing ends 619 from each other is provided. Generally, and preferably, the separation structures extend to a point lower than the dispensing end 619, or, in the conjunction with the use of capillaries 606, the tips thereof. In such a manner, a cone jet is allowed to form at the dispensing end of each nozzle structure 604.

The separation structure 614 may be made of any insulative material, such as Teflon, plastic, etc. Because the space charge effect is reduced by the separation structure 614, i.e., the space charge effect between nozzle structures, a more uniform dispersed spray of particles is provided. This is in part due to the lower voltage operation allowed with the use of such separation structure 614.

It will be recognized by one skilled in the art that the configuration of the separation structure 614 will be, at least in part, dependent upon the structure or configuration of the nozzle structures. In other words, if a rectangular pattern of nozzle structures is utilized, then line type separators may be used. Likewise, if a circular configuration of nozzle structures is used, then such separators may need to be in a type of circular configuration.

Separation structures are also shown in other embodiments previously described above. For example, in FIG. 11, separation extensions 558 are shown as extending from conductive plate structure 585 to separate the nozzle structures 556. Likewise, as shown in FIG. 9, separation extensions 512 extend from conductive plate structure 504 to separate the nozzle structures 506.

Figure 13:
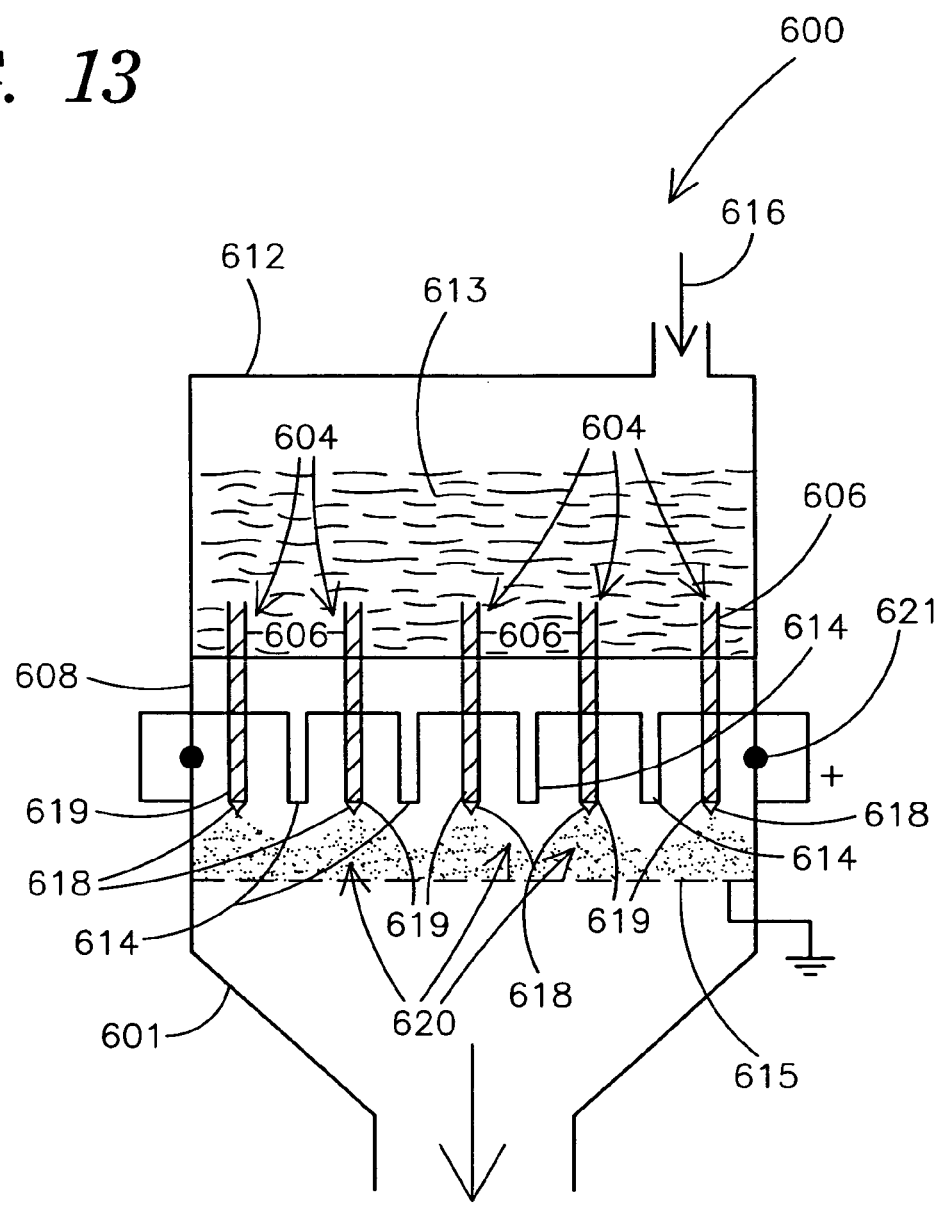
FIG. 13 is an alternate illustrative embodiment of a multiple nozzle electrospray dispensing device including separation structures provided between nozzles according to the present invention.

Also shown in FIG. 13 is a gas source 621 for providing a sheath within the housing 601 facilitate movement of the sprayed particles. For example, the gas source 621 may provide a gas sheath including an inert gas such as $CO_2$ or any other suitable gas such as previously described herein. Such a gas sheath may be used so as to allow for use of a higher electric field intensity without arcing, and further may be provided to carry away particles. Such gas sheaths may be provided in any of configurations described herein.

Figure 14B:
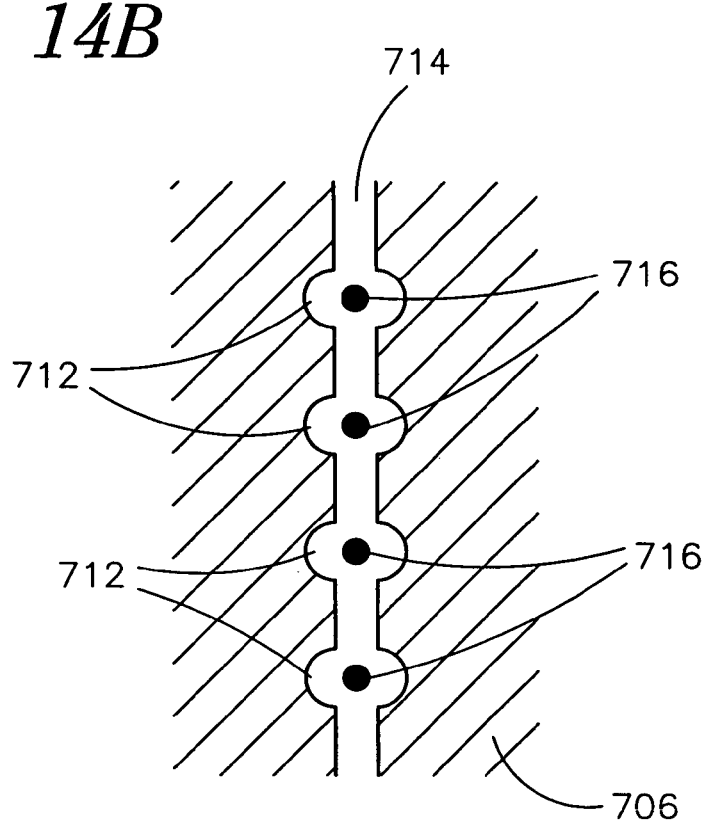
FIGS. 14A-14B are a side view and a cross sectional view, respectively, of an alternate electrospray dispensing apparatus that may be employed in the multiple nozzle particle generator system of FIG. 1 according to the present invention.
Figure 14A:
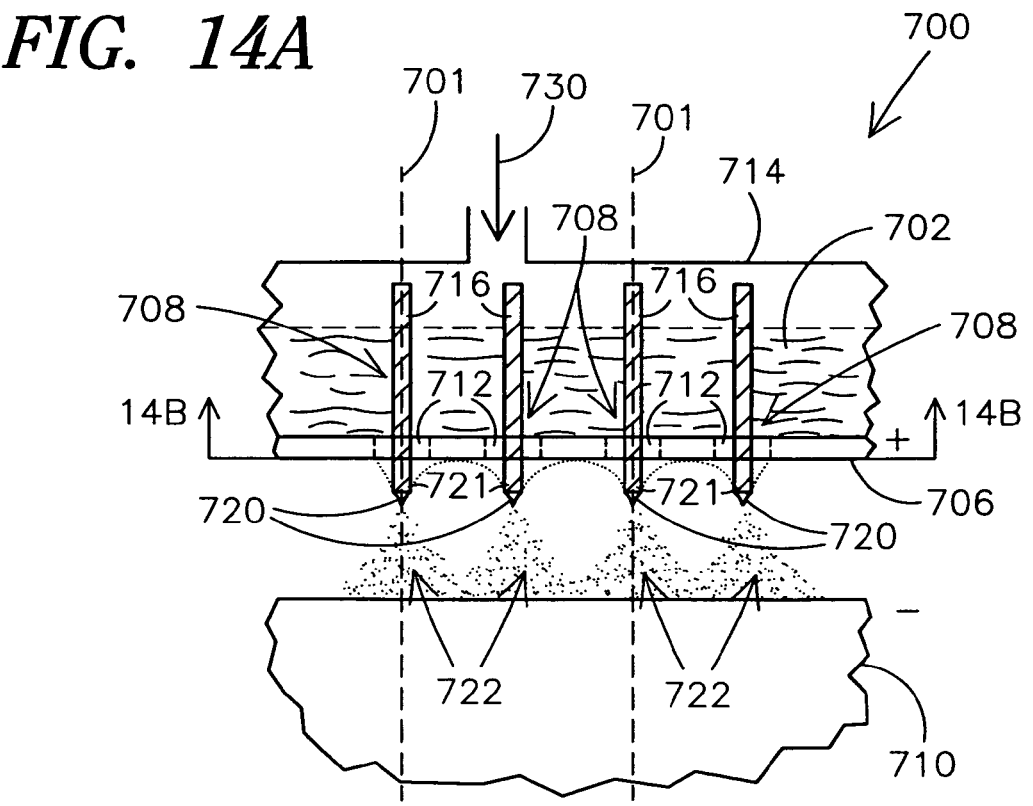

Another alternate dispensing device 700 is shown in FIGS. 14A-14B. In this alternate configuration, axial posts 716 are used to guide liquid flow. Cone jet formation is facilitated by having the guided post 716 at the center of the cone jet 720. FIG. 14A shows an exemplary side view of the dispensing device 700 and FIG. 14B shows a cross-section of FIG. 14A at line 14B-14B.

As shown in FIGS. 14A-14B, the dispensing device 700 includes a conductive plate 706 having multiple openings 712, e.g., circular openings, formed therein for use in providing multiple nozzle structures 708. Each opening 712 and the conductive plate 706 generally lie orthogonal to axes 701 of the nozzle structures 708. For machining purposes, such openings may be connected by channel portions 714.

Each of the nozzle structures 708 is formed using one of the openings 712 by providing a post member 716, e.g., a solid post, along the axis 701 through the center of the opening 712. The post member 716 includes a tip 721 that extends a predetermined distance past the conductive plate 706 and through the opening 712 to form the nozzle structure 708.

The plate structure 706 may form a part of fluid composition holding apparatus 704 in which fluid composition 702 is contained. As the fluid composition 702 is pushed through openings 712 forming part of the nozzle structure 708, by or under control of, for example, a compressed gas source 730, the fluid composition 702 follows the post 716. With the appropriate pressure applied by gas source 730 and an electrical potential difference applied between the plate 706 and target 710, cone jets 720 are formed at the tips 721 of the post members 716. Sprays of particles 722 are then provided as a result of the cone jets.

Figure 15A:
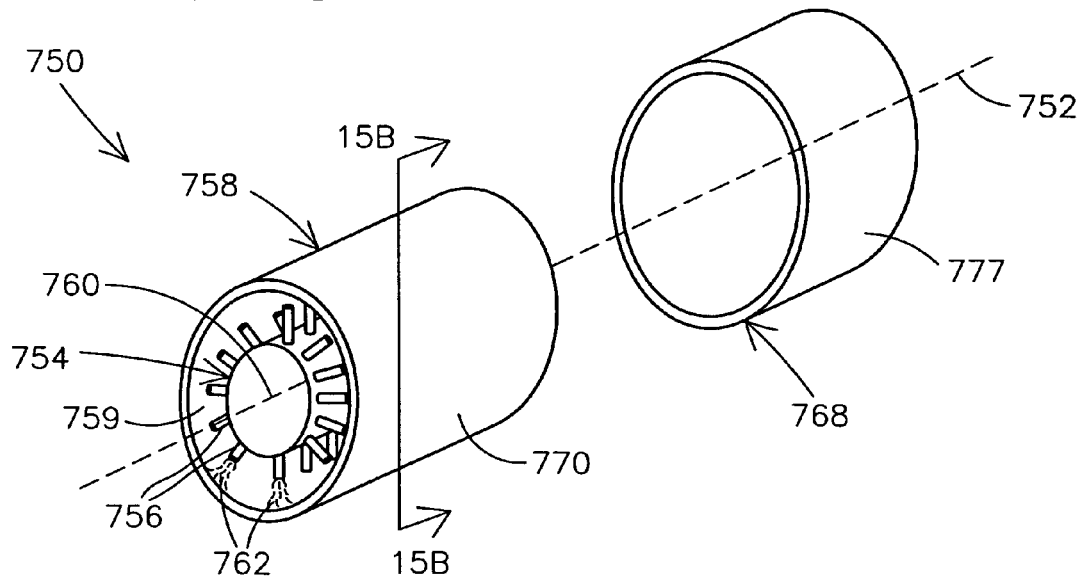
FIGS. 15A-15B show a perspective view and a cross sectional view, respectively, of one illustrative embodiment of a production system employing multiple nozzle structures according to the present invention.
Figure 15B:
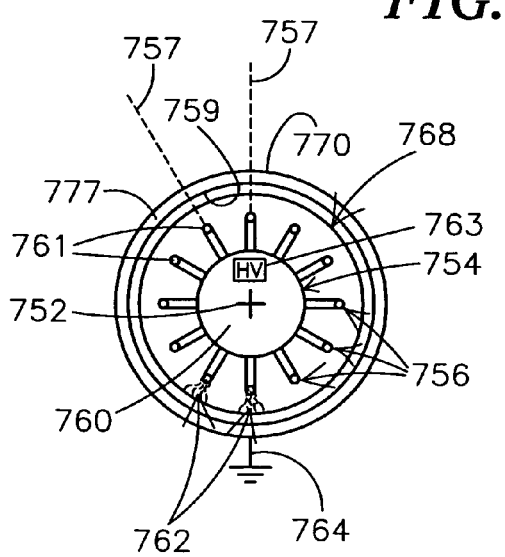

FIGS. 15A and 15B show an exemplary particle production system 750 for generating particles. FIG. 15A is a perspective view of the system 750, while FIG. 15B is a cross sectional view of the system 750 taken at line 15B-15B.

The production system 750 includes a dispensing device 760 located along axis 752. The dispensing apparatus 760 is a cylindrical fluid composition holding apparatus 754 having multiple nozzle structures 756 extending about the perimeter thereof. Each of the nozzle structures 756 extend along an axis 757 thereof which is orthogonal to the axis 752. As shown in FIG. 15B, the axis 757 of the multiple nozzle structures 757 lying in substantially the same plane orthogonal to the axis 752 are not parallel to one another. This is unlike the previous embodiments as described herein wherein each nozzle axis of the multiple nozzle structures were parallel, e.g., axes were aligned along the Z axis. This non-parallel configuration provides additional separation at the dispensing ends 761 of the nozzle structures 756. One will recognize that any of the nozzle structures previously described herein may be used in accordance with the embodiment of FIG. 15.

With the nozzle structures 756 provided and a high voltage 763 applied thereto, a nonuniform electric field is established between the nozzle structures 756 and an outer hollow cylindrical body 758 having an inner surface 759 and an opposing outer surface 770. As such, a cone jet is formed in the electric field at the dispensing end 761 of the nozzle structure 756 and sprays of particles 762 are provided onto the inner surface 759 of the cylindrical member 758.

With the sprayed particles on the inner surface 759 of the cylindrical member 758, a scraping apparatus 768 may be provided to remove such particles from the inner surface 759. This scraping apparatus 768 which extends along the axis 752 is also a cylindrical body sized to be slid through the cylindrical member 758 such that the outer surface 777 of the scraping apparatus 768 is in contact with the inner surface 759 of the cylindrical member 758 so as to remove, e.g., push, the nanoparticles off of the inner surface 759. The particles may then be collected.

One will recognize that this production system 750 is only but one embodiment of any numerous types of production and collection mechanisms that may be used to attain a quantity of particles desired. The present invention is in no manner limited to any particular collection devices.

Figure 16:
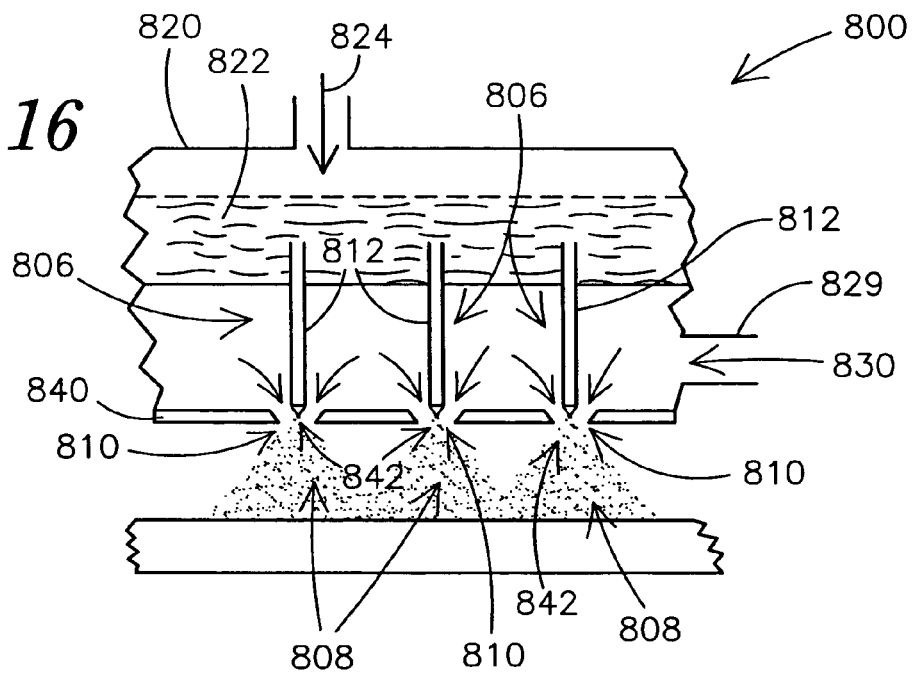
FIG. 16 show yet another alternate configuration of a multiple nozzle structure dispensing apparatus that forms cone jets for spraying particles using air as opposing to electrospray techniques and which may be employed in the particle generator system of FIG. 1 according to the present invention.
Figure 17:
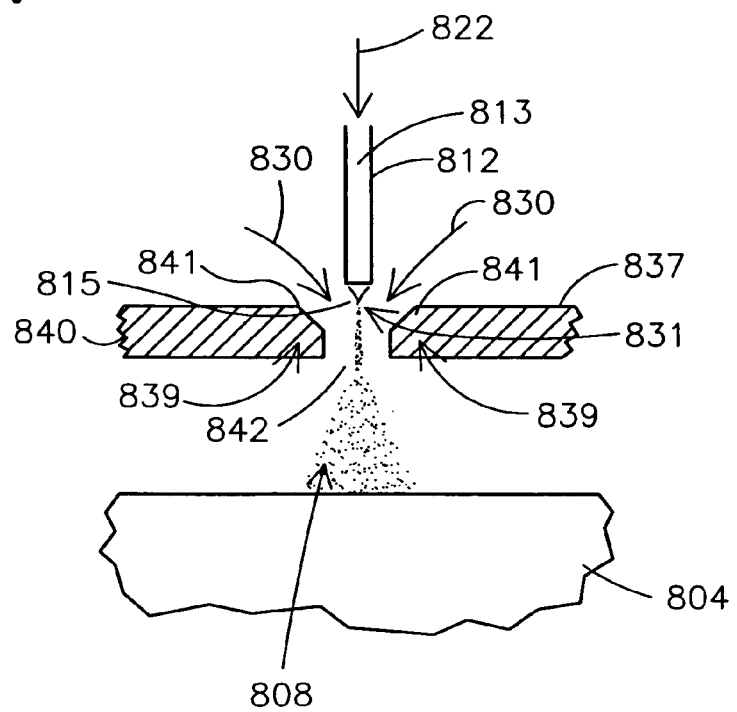
FIG. 17 shows a more detailed illustrative embodiment of a nozzle structure of the dispensing device of FIG. 16.

An alternative to providing a cone jet by electrostatic force is to form such a cone jet by using aerodynamic force. In such a manner, associated space charge problems of the spray of particles is eliminated. FIGS. 16 and 17 show an air dispensing device 800 that employs the use of aerodynamic force in the formation of a cone jet which may be employed in the general embodiment of the particle generator system shown in FIG. 1.

The air dispensing device 800 includes a plate 840 having openings 842 formed therein for use in providing multiple nozzle structures 806. The multiple nozzle structures s 806 of the air dispensing device 800 are provided by positioning a capillary 812 with an end 815 thereof in close proximity to the opening 842 in the plate 840. The capillary 812 generally lies orthogonal to the plate 840. In such a configuration and as further described below with reference to FIG. 17, a cone jet 831 can be formed at the dispensing end 810 of the nozzle structures 806 to provide a spray of particles 808 from each nozzle structure 806 onto target 804.

To form the cone jet 831, a fluid composition 822 held in holding apparatus 820 is provided into the capillaries 812 under control of, for example, compressed gas source 824. As the fluid composition 822 is pushed through the capillaries 812, a gas source 830, e.g., preferably a compressed gas source, provides compressed gas 830 around the dispensing tip 815 of capillary 812 and through opening 842 of each nozzle structure 806. At least in part, the cone jet mode is provided at the dispensing end 810 of each of the nozzle structures by the compressed gas 830 flowing through opening 842 and around the capillary tube tip 815 as further described below with reference to FIG. 17.

FIG. 17 shows a more detailed diagram of each nozzle structure 806 of the air dispensing device 800. As shown therein, the capillary tube 812 includes a body portion 813 and the tip 815. Preferably, the tip 815 is slightly tapered. The plate 840, which has the openings 842 defined therein, includes a tapered region 839 defining each opening 842. The tapered region 839 includes inner surfaces 841, i.e., inner relative to the compressed gas 830, provides for receiving the compressed gas 830 and applying aerodynamic force onto the meniscus of fluid composition 822 formed at capillary tube tip 815. The cone jet 831 is formed thereby which provides the spray of particles 808. It would be recognized that the tapered portion 839 may take one of various configurations.

For example, such tapered surfaces 841 may include multiple tapers or may be arced, or further, may even include multiple tapered inner and outer surfaces as previously described herein with reference to FIGS. 9-12.

Further, other structures in addition to capillaries may be used to provide the fluid composition in close proximity to the opening for 842. However, preferably, a capillary tube 812 having a tip 815 thereof positioned below the upper surface 837 and in the opening 842 defined in the plate 840 is employed.

Aerodynamic cone jets have been shown to produce particles having a size as small as 70 microns. For example, such cone jets are described in the article entitled "New Microfluidic Technologies to Generate Respirable Aerosols for Medical Application" by Afonso M. Ganan-Calvo, Journal of Aerosol Science, Vol. 30, Suppl. 1, pps. 541-542.

The dual capillary configurations or the dual structures such as those shown in FIGS. 8 and 11 may be implemented using the aerodynamic structures shown in FIGS. 16 and 17 as well. For example, multiple openings may be provided for each nozzle structure in a manner similar to that shown in FIG. 11. As such, for example, coated particles may be generated thereby.

All patents, patent documents, and references cited herein are incorporated in their entirety as if each were incorporated separately. This invention has been described with reference to illustrative embodiments and is not meant to be construed in a limiting sense. As described previously, one skilled in the art will recognize that other various illustrative applications may use the techniques as described herein to take advantage of the beneficial characteristics of the particles generated hereby. Various modifications of the illustrative embodiments, as well as additional embodiments to the invention, will be apparent to persons skilled in the art upon reference to this description.

What is claimed is:

1. An electrospraying method, the method comprising:
   providing a plurality of nozzle structures, wherein each nozzle structure comprises at least one opening defined along a center axis of the nozzle structure and terminating at a dispensing end thereof from which a spray of particles having an electrical charge applied thereto is dispensed, wherein the particles have a nominal diameter of about 1 nanometer to about 2000 nanometers, wherein the dispensing end of each nozzle structure is separated from the dispensing end of adjacent nozzle structures, and further wherein the dispensing end of a first nozzle structure terminates in a first plane orthogonal to the center axis of the nozzle structure and dispensing ends of one or more other nozzle structures terminate in one or more different planes than the first plane;
   dispensing the spray of particles from each nozzle structure by creating a nonuniform electrical field between the dispensing ends from which the sprays are established and an electrode electrically isolated from the dispensing ends; and
   depositing the particles on a surface to form a coating thereon.

2. The method of claim 1, wherein the surface upon which a coating is formed is part of a target structure positioned proximate the electrode electrically isolated from the dispensing ends, and further wherein the surface upon which the coating is formed lies between at least a portion of the electrode and the dispensing ends.

3. The method of claim 2, wherein the target structure comprises a tube.

4. The method of claim 1, wherein each of the nozzle structures comprises a capillary tube comprised of a body portion and a tapered capillary tip at the dispensing end of the capillary tube.

5. The method of claim 1, wherein each of the nozzle structures comprises a tapered portion used to define the opening, and further wherein at least a part of each of the nozzle structures extend from an integral multiple nozzle structure conductive portion.

6. The method of claim 1, wherein dispensing the spray of particles includes dispensing a spray of microdroplets comprising an active ingredient, and further wherein the electrical charge is concentrated on the active ingredient as the microdroplet evaporates.

7. The method of claim 1, wherein dispensing the spray of particles includes dispensing a spray of microdroplets comprising a particle, and further wherein the electrical charge is concentrated on the particle as the microdroplet evaporates, wherein the electrical charge of the microdroplet concentrated on the particle is in the range of about 80 percent to 95 percent of the Rayleigh charge limit for the microdroplet.

8. The method of claim 1, wherein the particles have a nominal diameter of about 1 nanometers to about 200 nanometers.

9. The method of claim 1, wherein each of the nozzle structures comprise at least a first and second opening terminating at the dispensing end of each nozzle structure.

10. The method of claim 9, wherein the method further comprises:
    providing a first flow of a first fluid composition at the first opening;
    providing a second flow of a second fluid composition at the second opening; and
    establishing a spray of particles from the first and second fluid compositions.

11. The method of claim 1, wherein the method further comprises:
    providing a charged pattern; and
    collecting the spray of particles on the charged pattern.

12. The method of claim 1, wherein depositing the particles on a surface to form a coating thereon comprises depositing a plurality of layers on the surface.

13. The method of claim 1, wherein providing a plurality of nozzle structures comprises providing a circular configuration of nozzle structures comprising an outer multiple nozzle structure ring and one or more inner multiple nozzle structure rings, wherein each of the outer multiple nozzle structure rings and the inner multiple nozzle structure rings are concentric about a center nozzle structure, and further wherein each of the nozzle structures of the one or more inner multiple nozzle structure rings are at a substantially equal internozzle distance (L) from adjacent nozzle structure.

14. The method of claim 1, wherein the dispensing ends of the plurality of nozzle structures form a configuration with the dispensing end of the first nozzle structure lying in the first plane orthogonal to the center axis thereof and at least one or more other dispensing ends of the plurality nozzle structures lying in at least a second plane different from the first plane and orthogonal to the center axis of the first nozzle structure.

15. The method of claim 1, wherein the center axes of two or more nozzle structures are not parallel to one another.

16. An electrospraying method, the method comprising:
    providing a plurality of nozzle structures, wherein each nozzle structure comprises at least two openings defined along a center axis of the nozzle structure and terminating at a dispensing end thereof from which a spray of particles having an electrical charge applied thereto is dispensed, wherein the at least two openings comprise at least a first and second opening terminating at the dispensing end of each nozzle structure, wherein the dispensing end of a first nozzle structure terminates in a first plane orthogonal to the center axis of the nozzle structure, and further wherein the dispensing ends of one or more other nozzle structures terminate in one or more different planes than the first plane;

providing a first flow of a first fluid composition at the first opening;

providing a second flow of a second fluid composition at the second opening;

dispensing the spray of particles from each nozzle structure using the first and second fluid compositions by creating a nonuniform electrical field between the dispensing ends from which the sprays are established and an electrode electrically isolated from the dispensing ends, wherein the particles have a nominal diameter of about 1 nanometer to about 2000 nanometers, and further wherein dispensing the spray of particles comprises dispensing a spray of microdroplets comprising an active ingredient, wherein the electrical charge is concentrated on the active ingredient as the microdroplet evaporates;

providing a target structure comprising a surface upon which a coating is to be formed, wherein the target structure is positioned proximate the electrode electrically isolated from the dispensing ends, and further wherein the surface upon which the coating is to be formed lies between at least a portion of the electrode and the dispensing ends; and depositing the particles on the surface of the target structure to form a coating thereon.

17. The method of claim 16, wherein the target structure comprises a tube.

18. The method of claim 16, wherein each of the nozzle structures comprises a capillary tube comprised of a body portion and a tapered capillary tip at the dispensing end of the capillary tuba.

19. The method of claim 16, wherein each of the nozzle structures comprises a tapered portion used to define the opening, and further wherein at least a part of each of the nozzle structures extend from an integral multiple nozzle structure conductive portion.

20. The method of claim 16, wherein the electrical charge of the microdroplet concentrated on the particle is in the range of about 80 percent to 95 percent of the Rayleigh charge limit for the microdroplet.

21. The method of claim 16, wherein the particles have a nominal diameter of about 1 nanometers to about 200 nanometers.

22. The method of claim 16, wherein the method further comprises:

providing a charged pattern; and collecting the spray of particles on the charged pattern.

23. The method of claim 16, wherein depositing the particles on a surface to form a coating thereon comprises depositing a plurality of layers on the surface.

24. The method of claim 16, wherein providing a plurality of nozzle structures comprises providing a circular configuration of nozzle structures comprising an outer multiple nozzle structure ring and one or more inner multiple nozzle structure rings, wherein each of the outer multiple nozzle structure rings and the inner multiple nozzle structure rings are concentric about a center nozzle structure, and further wherein each of the nozzle structures of the one or more inner multiple nozzle structure rings are at a substantially equal internozzle distance (L) from adjacent nozzle structures.

25. The method of claim 16, wherein the dispensing ends of the plurality of nozzle structures form a configuration with the dispensing end of the first nozzle structure lying in the first plane orthogonal to the center axis thereof and at least one or more other dispensing ends of the plurality nozzle structures lying in at least a second plane different from the first plane and orthogonal to the center axis of the first nozzle structure.

26. The method of claim 16, wherein the center axes of two or more nozzle structures are not parallel to one another.

27. An electrospraying method, the method comprising:

providing a plurality of nozzle structures, wherein each of the plurality of nozzle structures comprises at least two openings defined along a center axis of the nozzle structure and terminating at a dispensing end thereof from which a spray of particles having an electrical charge applied thereto is dispensed, wherein the at least two openings comprise at least a first and second opening terminating at the dispensing end of the at least one nozzle structure, wherein the dispensing end of a first nozzle structure terminates in a first plane orthogonal to the center axis of the nozzle structure, and further wherein dispensing ends of one or more other nozzle structures terminate in one or more different planes than the first plane;

providing a first flow of a first fluid composition at the first opening;

providing a second flow of a second fluid composition at the second opening;

dispensing the spray of particles from the plurality of nozzle structures using the first and second fluid compositions by creating a nonuniform electrical field between the dispensing ends from which the spray is established and an electrode electrically isolated from the dispensing ends, wherein the particles have a nominal diameter of about 1 nanometer to about 2000 nanometers;

providing a target structure comprising a surface upon which a coating is to be formed; and depositing the particles on the surface of the target structure to form a coating thereon.

28. The method of claim 27, wherein the target structure is positioned proximate the electrode electrically isolated from the dispensing ends, and further wherein the surface upon which the coating is to be formed lies between at least a portion of the electrode and the dispensing ends.

29. The method of claim 27, wherein the target structure comprises a tube.

30. The method of claim 27, wherein each of the nozzle structures comprises a capillary tube comprised of a body portion and a tapered capillary tip at the dispensing end of the capillary tube.

31. The method of claim 27, wherein each of the nozzle structures comprises a tapered portion used to define the opening, and further wherein at least a part of each of the nozzle structures extend from an integral multiple nozzle structure conductive portion.

32. The method of claim 27, wherein dispensing the spray of particles comprises dispensing a spray of microdroplets comprising an active ingredient, wherein the electrical charge is concentrated on the active ingredient as the microdroplet evaporates.

33. The method of claim 32, wherein the electrical charge of the microdroplet concentrated on the particle is in the range of about 80 percent to 95 percent of the Rayleigh charge limit for the microdroplet.

34. The method of claim 27, wherein the particles have a nominal diameter of about 1 nanometers to about 200 nanometers.

35. The method of claim 27, wherein the method further comprises:

providing a charged pattern; and collecting the spray of particles on the charged pattern.

36. The method of claim 27, wherein depositing the particles on the surface to form a coating thereon comprises depositing a plurality of layers on the surface.

37. The method of claim 27, wherein providing a plurality of nozzle structures comprises providing a circular configuration of nozzle structures comprising an outer multiple nozzle structure ring and one or more inner multiple nozzle structure rings, wherein each of the outer multiple nozzle structure rings and the inner multiple nozzle structure rings are concentric about a center nozzle structure, and further wherein each of the nozzle structures of the one or more inner multiple nozzle structure rings are at a substantially equal internozzle distance (L) from adjacent nozzle structures.

38. The method of claim 27, wherein the dispensing ends of the plurality of nozzle structures form a configuration with the dispensing end of the first nozzle structure lying in the first plane orthogonal to the center axis thereof and at least one or more other dispensing ends of the plurality nozzle structures lying in at least a second plane different from the first plane and orthogonal to the center axis of the first nozzle structure.

39. The method of claim 27, wherein the center axes of two or more nozzle structures are not parallel to one another.

* * * * *